(12) United States Patent
Ash et al.

(10) Patent No.: US 8,945,936 B2
(45) Date of Patent: Feb. 3, 2015

(54) MEASURING CHEMICAL PROPERTIES OF A SAMPLE FLUID IN DIALYSIS SYSTEMS

(75) Inventors: Stephen R. Ash, Lafayette, IN (US); Thomas A. Sullivan, Pine Village, IN (US); David Carr, West Lafayette, IN (US); Michael James Beiriger, Pittsburgh, PA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 537 days.

(21) Appl. No.: 13/080,745

(22) Filed: Apr. 6, 2011

(65) Prior Publication Data
US 2012/0258545 A1 Oct. 11, 2012

(51) Int. Cl.
*G01N 31/22* (2006.01)
*G01N 21/05* (2006.01)
*A61M 1/16* (2006.01)
*G01N 33/49* (2006.01)
*G01N 21/3504* (2014.01)
*A61M 1/36* (2006.01)

(52) U.S. Cl.
CPC ......... *A61M 1/1658* (2013.01); *G01N 33/4925* (2013.01); *G01N 21/3504* (2013.01); *A61M 1/1607* (2014.01); *A61M 1/1609* (2014.01); *A61M 1/3612* (2014.01); *A61M 1/1696* (2013.01); *A61M 2205/3306* (2013.01); *A61M 2205/3324* (2013.01); *A61M 2230/202* (2013.01); *A61M 2230/208* (2013.01)
USPC ............. 436/133; 436/52; 436/108; 436/113; 436/163; 436/165

(58) Field of Classification Search
USPC ............................ 436/52, 108, 113, 133, 163
See application file for complete search history.

(56) References Cited

U.S. PATENT DOCUMENTS

| 3,781,910 | A | | 12/1973 | Herrmann | |
|---|---|---|---|---|---|
| 3,926,734 | A | * | 12/1975 | Gray et al. | 435/12 |
| 3,973,912 | A | * | 8/1976 | Trafton et al. | 436/68 |
| 3,992,109 | A | * | 11/1976 | Bock | 356/410 |
| 4,003,705 | A | * | 1/1977 | Buzza et al. | 436/68 |
| 4,003,707 | A | * | 1/1977 | Lubbers et al. | 436/172 |
| 4,019,862 | A | * | 4/1977 | Dahms | 436/68 |
| 4,029,597 | A | * | 6/1977 | Neisius et al. | 436/163 |

(Continued)

FOREIGN PATENT DOCUMENTS

| CN | 2854581 | 1/2007 | G01N 21/31 |
|---|---|---|---|
| CN | 1991337 | 7/2007 | G01N 21/31 |

(Continued)

OTHER PUBLICATIONS

Rosenberg, E. et al, Fresenius Journal of Analytical Chemistry 1994, 348, 530-532.*

(Continued)

*Primary Examiner* — Arlen Soderquist
(74) *Attorney, Agent, or Firm* — Fish & Richardson P.C.

(57) ABSTRACT

In one aspect of the invention, a method includes determining an amount of carbon dioxide ($CO_2$) in dialysate flowing through a dialysis system using a $CO_2$ sensor associated with the dialysis system, determining, using a pH sensor associated with the dialysis system, a pH level of the dialysate, and calculating a level of bicarbonate in the dialysate based at least in part on the determined amount of $CO_2$ measured in the gas and the determined pH level of the dialysate.

49 Claims, 9 Drawing Sheets

(56) References Cited

U.S. PATENT DOCUMENTS

| | | | |
|---|---|---|---|
| 4,033,330 A * | 7/1977 | Willis et al. ............... 600/366 |
| 4,041,932 A * | 8/1977 | Fostick ...................... 600/326 |
| 4,139,348 A | 2/1979 | Swartz |
| 4,153,554 A * | 5/1979 | von der Heide et al. ..... 210/96.2 |
| 4,166,804 A * | 9/1979 | Bleha et al. ................. 436/163 |
| 4,201,548 A * | 5/1980 | Tamaoku et al. ............ 436/113 |
| 4,244,787 A * | 1/1981 | Klein et al. .................. 205/778 |
| 4,299,794 A * | 11/1981 | Kelley et al. .............. 422/82.13 |
| 4,427,889 A * | 1/1984 | Muller .................... 250/339.11 |
| 4,471,220 A | 9/1984 | Perry et al. |
| 4,661,246 A * | 4/1987 | Ash .............................. 210/87 |
| 4,663,724 A * | 5/1987 | Onizuka et al. ............... 702/24 |
| 4,677,077 A * | 6/1987 | Onizuka et al. .............. 436/50 |
| 4,705,669 A * | 11/1987 | Tsuji et al. .................... 422/93 |
| 4,973,561 A * | 11/1990 | Hansen et al. ................ 436/52 |
| 5,059,397 A * | 10/1991 | Melly et al. ................... 422/94 |
| 5,102,805 A | 4/1992 | Baughman et al. |
| 5,133,937 A * | 7/1992 | Frackleton et al. ............ 422/81 |
| 5,155,545 A | 10/1992 | Rinke |
| 5,230,702 A * | 7/1993 | Lindsay et al. ............. 604/4.01 |
| 5,258,314 A * | 11/1993 | Skerratt ...................... 436/165 |
| 5,308,315 A * | 5/1994 | Khuri et al. ................ 604/4.01 |
| 5,313,941 A * | 5/1994 | Braig et al. ................. 600/322 |
| 5,394,236 A | 2/1995 | Murnick |
| 5,403,746 A | 4/1995 | Bentsen et al. |
| 5,409,612 A * | 4/1995 | Maltais et al. ............... 210/636 |
| 5,442,969 A * | 8/1995 | Troutner et al. ............ 73/863.71 |
| 5,479,019 A * | 12/1995 | Gross ......................... 250/345 |
| 5,494,640 A * | 2/1996 | Simon et al. .............. 422/82.05 |
| 5,507,723 A * | 4/1996 | Keshaviah ................. 604/6.11 |
| 5,518,623 A * | 5/1996 | Keshaviah et al. ........... 210/646 |
| 5,544,186 A | 8/1996 | Sauer et al. |
| 5,553,616 A * | 9/1996 | Ham et al. .................. 600/316 |
| 5,633,169 A * | 5/1997 | Young et al. .................. 436/68 |
| 5,648,269 A * | 7/1997 | Lakowicz et al. .............. 436/68 |
| 5,660,790 A * | 8/1997 | Lawrence et al. ............ 422/426 |
| 5,670,057 A * | 9/1997 | Chen et al. .................. 210/739 |
| 5,685,988 A * | 11/1997 | Malchesky ................... 210/646 |
| 5,698,083 A * | 12/1997 | Glass ...................... 204/403.03 |
| 5,709,839 A * | 1/1998 | Dobson ......................... 422/81 |
| 5,725,773 A * | 3/1998 | Polaschegg .................. 210/636 |
| 5,744,031 A * | 4/1998 | Bene ........................ 210/321.71 |
| 5,754,288 A | 5/1998 | Yamamoto et al. |
| 5,788,647 A | 8/1998 | Eggers |
| 5,788,846 A * | 8/1998 | Sternby ....................... 210/647 |
| 5,817,007 A * | 10/1998 | Fodgaard et al. ............. 600/322 |
| 5,837,199 A | 11/1998 | Dumschat |
| 5,838,008 A | 11/1998 | Esler et al. |
| 5,849,179 A * | 12/1998 | Emerson et al. ............... 210/87 |
| 5,858,186 A * | 1/1999 | Glass ....................... 205/777.5 |
| 5,892,586 A | 4/1999 | Thony et al. |
| 5,908,789 A * | 6/1999 | Weckstrom .................. 436/133 |
| 5,964,712 A | 10/1999 | Kubo et al. |
| 6,110,384 A * | 8/2000 | Goux et al. .................. 210/739 |
| 6,126,831 A * | 10/2000 | Goldau et al. ............... 210/646 |
| 6,143,246 A * | 11/2000 | Lee et al. ...................... 422/62 |
| 6,186,958 B1 * | 2/2001 | Katzman et al. ............. 600/532 |
| 6,190,858 B1 * | 2/2001 | Persaud et al. .................. 435/4 |
| 6,212,424 B1 * | 4/2001 | Robinson .................... 600/475 |
| 6,219,567 B1 * | 4/2001 | Eggers et al. ................ 600/322 |
| 6,230,545 B1 | 5/2001 | Adolph et al. |
| 6,246,894 B1 * | 6/2001 | Steuer et al. ................. 600/322 |
| 6,258,027 B1 * | 7/2001 | Sternby ....................... 600/366 |
| 6,280,634 B1 * | 8/2001 | Shah et al. ................... 210/739 |
| 6,287,851 B1 * | 9/2001 | Delwiche et al. .......... 435/287.5 |
| 6,306,347 B1 * | 10/2001 | Mason et al. ................ 422/417 |
| 6,368,870 B1 | 4/2002 | Harp |
| 6,379,969 B1 | 4/2002 | Mauze et al. |
| 6,444,435 B1 * | 9/2002 | Christner et al. ............... 435/14 |
| 6,455,851 B1 | 9/2002 | Lord et al. |
| 6,527,398 B1 | 3/2003 | Fetzer |
| 6,555,058 B2 * | 4/2003 | Kamibayashi et al. ......... 422/44 |
| 6,602,716 B1 | 8/2003 | Kliment |
| 6,605,471 B1 * | 8/2003 | Lundsgaard et al. ......... 436/165 |
| 6,648,845 B1 * | 11/2003 | Gotch et al. ................ 604/5.01 |
| 6,666,840 B1 * | 12/2003 | Falkvall et al. .............. 604/5.04 |
| 6,702,774 B1 * | 3/2004 | Polaschegg .................. 604/5.01 |
| 6,758,975 B2 * | 7/2004 | Peabody et al. .............. 210/645 |
| 6,861,266 B1 * | 3/2005 | Sternby ....................... 436/178 |
| 6,913,590 B2 * | 7/2005 | Sorenson et al. ............... 604/29 |
| 6,939,471 B2 * | 9/2005 | Gross et al. .................. 210/746 |
| 7,002,670 B2 * | 2/2006 | Wariar et al. .................. 356/39 |
| 7,326,576 B2 * | 2/2008 | Womble et al. .............. 436/108 |
| 7,435,342 B2 * | 10/2008 | Tsukamoto .................. 210/195.2 |
| 7,488,447 B2 * | 2/2009 | Sternby ......................... 422/44 |
| 7,608,042 B2 * | 10/2009 | Goldberger et al. .......... 600/366 |
| 7,613,488 B1 | 11/2009 | Maracas et al. |
| 7,662,637 B2 * | 2/2010 | Godec ......................... 436/146 |
| 7,744,554 B2 * | 6/2010 | Howard ...................... 604/6.11 |
| 7,776,210 B2 * | 8/2010 | Rosenbaum et al. ........ 210/96.2 |
| 7,867,214 B2 * | 1/2011 | Childers et al. .............. 604/411 |
| 8,057,679 B2 * | 11/2011 | Yu et al. ...................... 210/645 |
| 8,080,161 B2 * | 12/2011 | Ding et al. ............... 210/321.71 |
| 8,328,758 B2 * | 12/2012 | Childers et al. .............. 604/131 |
| 8,377,308 B2 * | 2/2013 | Kreymann et al. ........... 210/639 |
| 8,409,864 B2 * | 4/2013 | Ash ............................ 436/113 |
| 2001/0012539 A1 | 8/2001 | Barnard et al. |
| 2001/0018206 A1 * | 8/2001 | Delwiche et al. .......... 435/287.5 |
| 2002/0020206 A1 * | 2/2002 | Mason et al. ................... 73/1.02 |
| 2002/0031447 A1 | 3/2002 | Brinz et al. |
| 2002/0123715 A1 * | 9/2002 | Sorenson et al. ............... 604/29 |
| 2002/0158202 A1 | 10/2002 | Webber et al. |
| 2002/0197708 A1 | 12/2002 | Bachur |
| 2003/0078518 A1 | 4/2003 | Skover |
| 2003/0080295 A1 | 5/2003 | Webber et al. |
| 2003/0092008 A1 | 5/2003 | Bell et al. |
| 2003/0111607 A1 | 6/2003 | Bachur et al. |
| 2003/0112019 A1 | 6/2003 | Forster et al. |
| 2003/0113931 A1 * | 6/2003 | Pan et al. .................... 436/113 |
| 2003/0113932 A1 * | 6/2003 | Sternberg et al. ............ 436/113 |
| 2003/0134427 A1 | 7/2003 | Roller et al. |
| 2003/0199742 A1 | 10/2003 | Braig et al. |
| 2003/0216677 A1 | 11/2003 | Pan et al. |
| 2004/0019312 A1 * | 1/2004 | Childers et al. ............. 604/4.01 |
| 2004/0077093 A1 | 4/2004 | Pan |
| 2004/0115319 A1 | 6/2004 | Morris et al. |
| 2004/0121478 A1 | 6/2004 | Brinz et al. |
| 2004/0188622 A1 * | 9/2004 | Yokura et al. ................ 250/343 |
| 2004/0206906 A1 | 10/2004 | Owen |
| 2004/0211905 A1 | 10/2004 | Hancock et al. |
| 2004/0262222 A1 | 12/2004 | Chordia et al. |
| 2005/0101901 A1 * | 5/2005 | Gura ........................... 604/5.02 |
| 2005/0106650 A1 * | 5/2005 | Godec ........................... 435/12 |
| 2005/0150832 A1 * | 7/2005 | Tsukamoto .................. 210/638 |
| 2005/0274658 A1 * | 12/2005 | Rosenbaum et al. ........ 210/96.2 |
| 2006/0024720 A1 | 2/2006 | McLean et al. |
| 2006/0043301 A1 | 3/2006 | Mantele et al. |
| 2006/0046275 A1 | 3/2006 | Collier et al. |
| 2006/0119851 A1 | 6/2006 | Bounaix |
| 2006/0157413 A1 * | 7/2006 | Bene et al. ................... 210/646 |
| 2006/0188407 A1 | 8/2006 | Gable et al. |
| 2006/0276697 A1 | 12/2006 | Demuth et al. |
| 2007/0007184 A1 * | 1/2007 | Voto et al. ..................... 210/85 |
| 2007/0088333 A1 * | 4/2007 | Levin et al. ................ 604/890.1 |
| 2007/0102654 A1 | 5/2007 | Schoo |
| 2007/0110621 A1 | 5/2007 | MacIntyre et al. |
| 2007/0134751 A1 | 6/2007 | Petrich et al. |
| 2007/0161113 A1 * | 7/2007 | Ash ............................ 436/113 |
| 2007/0177130 A1 | 8/2007 | MacIntyre et al. |
| 2008/0179530 A1 | 7/2008 | Liu et al. |
| 2008/0198361 A1 | 8/2008 | Kaushal et al. |
| 2008/0217245 A1 * | 9/2008 | Rambod et al. ............. 210/637 |
| 2008/0255769 A1 | 10/2008 | Zhou et al. |
| 2008/0286154 A1 | 11/2008 | Kane |
| 2009/0127193 A1 * | 5/2009 | Updyke et al. ............... 210/636 |
| 2009/0164138 A1 | 6/2009 | Goto et al. ..................... 702/24 |
| 2009/0173682 A1 * | 7/2009 | Robinson et al. ............ 210/232 |
| 2009/0191092 A1 | 7/2009 | Burke et al. |
| 2009/0198170 A1 * | 8/2009 | Childers et al. ............. 604/6.09 |
| 2009/0248350 A1 * | 10/2009 | Yamakage et al. ........... 702/134 |
| 2009/0299154 A1 | 12/2009 | Segman |
| 2010/0051552 A1 * | 3/2010 | Rohde et al. ................ 210/647 |
| 2010/0114012 A1 * | 5/2010 | Sandford et al. ............... 604/28 |
| 2010/0133100 A1 | 6/2010 | Scarano .................... 204/403.01 |

(56) References Cited

U.S. PATENT DOCUMENTS

2010/0140149 A1*  6/2010  Fulkerson et al. .............. 210/85
2010/0252490 A1* 10/2010  Fulkerson et al. ........... 210/96.2
2010/0312172 A1* 12/2010  Hoffman ........................ 604/28
2012/0248017 A1* 10/2012  Beiriger et al. ............... 210/143

FOREIGN PATENT DOCUMENTS

| | | | |
|---|---|---|---|
| DE | 2825134 | 12/1978 | |
| DE | 198 15 273 | 10/1998 | ............ G01N 21/35 |
| EP | 0532433 | 3/1993 | |
| EP | 0 578 630 | 1/1994 | ............ G01N 21/77 |
| EP | 1163917 | 12/2001 | |
| EP | 1319417 | 6/2003 | |
| WO | 03/010510 | 2/2003 | |
| WO | 03/069316 | 8/2003 | ............ G01N 21/39 |
| WO | 2006/125198 | 11/2006 | |
| WO | 2007/142644 | 12/2007 | ............... A61B 5/08 |
| WO | 2008/003328 | 1/2008 | ............ G01N 21/35 |
| WO | 2008/079032 | 7/2008 | |
| WO | 2009/082213 | 7/2009 | ............ G01N 21/77 |
| WO | 2009/123461 | 10/2009 | ............ H01S 5/343 |

OTHER PUBLICATIONS

Radomska, A. et al, Analyst 2001, 126, 1564-1567.*
Olesberg, J. T. et al, Clinical Chemistry 2004, 50, 175-181.*
Notification concerning Transmittal of International Preliminary Report on Patentability and Written Opinion from corresponding PCT Application No. PCT/US2012/031840, mailed Oct. 17, 2013, 12 pages.

* cited by examiner

MEASURING CHEMICAL PROPERTIES OF A SAMPLE FLUID IN DIALYSIS SYSTEMS

TECHNICAL FIELD

This invention relates to measuring chemical properties of a sample fluid in dialysis systems.

BACKGROUND

Dialysis is a treatment used to support a patient with insufficient renal function. The two principal dialysis methods are hemodialysis and peritoneal dialysis.

During hemodialysis ("HD"), the patient's blood is passed through a dialyzer of a dialysis machine while also passing a dialysis solution or dialysate through the dialyzer. A semipermeable membrane in the dialyzer separates the blood from the dialysate within the dialyzer and allows diffusion and osmosis exchanges to take place between the dialysate and the blood stream. These exchanges across the membrane result in the removal of waste products, including solutes like urea and creatinine, from the blood. These exchanges also regulate the levels of other substances, such as sodium and water, in the blood. In this way, the dialysis machine acts as an artificial kidney for cleansing the blood.

During peritoneal dialysis ("PD"), a patient's peritoneal cavity is periodically infused with sterile aqueous solution, referred to as PD solution or dialysate. The membranous lining of the patient's peritoneum acts as a natural semipermeable membrane that allows diffusion and osmosis exchanges to take place between the solution and the blood stream. These exchanges across the patient's peritoneum result in the removal of waste products, including solutes like urea and creatinine, from the blood, and regulate the levels of other substances, such as sodium and water, in the blood.

Many PD machines are designed to automatically infuse, dwell, and drain dialysate to and from the patient's peritoneal cavity. The treatment typically lasts for several hours, often beginning with an initial drain cycle to empty the peritoneal cavity of used or spent dialysate. The sequence then proceeds through the succession of fill, dwell, and drain phases that follow one after the other. Each phase is called a cycle.

SUMMARY

In one aspect of the invention, a method includes determining an amount of carbon dioxide ($CO_2$) in dialysate flowing through a dialysis system using a $CO_2$ sensor associated with the dialysis system, determining, using a pH sensor associated with the dialysis system, a pH level of the dialysate, and calculating a level of bicarbonate in the dialysate based at least in part on the determined amount of $CO_2$ measured in the gas and the determined pH level of the dialysate.

In another aspect of the invention, a method includes extracting a first portion of fluid from a fluid circuit of a dialysis system, causing the first portion of fluid to flow through a first channel into a first chamber that contains a composition to liberate a first CO2 gas from the first portion of fluid, determining a level of total CO2 in the first portion of fluid based at least in part on the first CO2 gas, extracting a second portion of fluid from the fluid circuit of the dialysis system, causing the second portion of the first portion of fluid to flow through a second channel into a second chamber to liberate a second CO2 gas from the second portion of fluid, and determining a level of total urea in the second portion of fluid based at least in part on the second CO2 gas.

In an additional aspect of the invention, a dialysis system includes a dialysis machine including a pH sensor and a CO2 sensor, and a dialysis fluid chamber configured to be connected to the dialysis machine. The dialysis fluid chamber includes a housing defining an inlet port, an outlet port, a dialysis fluid passage extending between the inlet and outlet ports, and first and second apertures adjacent the fluid passage, a pH reactive material disposed over the first aperture of the housing, and a gas-permeable membrane disposed over the second aperture of the housing. The pH reactive material and the gas-permeable membrane align with the pH sensor and CO2 sensor, respectively, when the dialysis fluid chamber is connected to the dialysis machine such that the pH sensor and CO2 sensor can be used to detect a pH level and CO2 level, respectively, of a dialysis fluid flowing through the dialysis fluid chamber.

In an additional aspect of the invention, a dialysis fluid chamber includes a housing defining an inlet port, an outlet port, a dialysis fluid passage extending between the inlet and outlet ports, and first and second apertures adjacent the fluid passage, a pH reactive material disposed over the first aperture of the housing, and a gas-permeable membrane disposed over the second aperture of the housing. The dialysis fluid chamber is configured such that the pH reactive material and the gas-permeable membrane align with a pH sensor and CO2 sensor, respectively, of a dialysis machine when the dialysis fluid chamber is connected to the dialysis machine.

In an additional aspect of the invention, a dialysis system includes a dialysis machine including a sensor, and a gas emission device configured to be connected to the dialysis machine in a manner such that dialysis fluid can be forced into the gas emission device. The gas emission device includes a housing defining first and second chambers, and a member defining a first fluid passage leading to the first chamber and a second fluid passage leading to the second chamber, at least one of the first and second fluid passages being heated such that dialysis fluid flowing along the at least one of the first and second fluid passages is heated to a desired temperature. The first chamber contains an acid that causes $CO_2$ to be emitted from dialysis fluid that is delivered to the first chamber via the first fluid passage, the second chamber can cause a gas to be emitted from dialysis fluid that is delivered to the second chamber via the second fluid passage, and the sensor is configured to detect an amount of $CO_2$ emitted from the dialysis fluid delivered to the first chamber and to detect an amount of the gas emitted from the dialysis fluid delivered to the second chamber.

In an additional aspect of the invention, a gas emission device is configured to be connected to a dialysis machine in a manner such that dialysis fluid can be forced into the gas emission device. The gas emission device includes a housing defining first and second chambers, and a member defining a first fluid passage leading to the first chamber and a second fluid passage leading to the second chamber, at least one of the first and second fluid passages being heated such that dialysis fluid flowing along the at least one of the first and second fluid passages is heated to a desired temperature. The first chamber contains an acid that causes CO2 to be emitted from dialysis fluid that is delivered to the first chamber via the first fluid passage, the second chamber can cause a gas to be emitted from dialysis fluid that is delivered to the second chamber via the second fluid passage, and the gas emission device defines a flute portion that is positioned adjacent a sensor of the dialysis machine when the gas emission device is connected to the dialysis machine.

In an additional aspect of the invention, a method includes extracting a first portion of fluid from a fluid circuit of a dialysis system, causing the first portion of fluid to flow through a first channel into a first chamber that contains a composition to liberate a CO2 gas from the first portion of fluid, determining a level of total CO2 in the first portion of fluid based at least in part on the CO2 gas, extracting a second portion of fluid from the fluid circuit of the dialysis system, causing the second portion of the first portion of fluid to flow through a second channel into a second chamber to liberate a NH3 gas from the second portion of fluid, and determining a level of total urea in the second portion of fluid based at least in part on the NH3 gas.

Implementations can include one or more of the following features.

In some implementations, dialysate is caused to flow into a chamber that includes a gas-permeable membrane.

In some implementations, the membrane is configured to prevent liquid from passing through the membrane.

In some implementations, the $CO_2$ sensor includes an infrared sensor.

In some implementations, dialysate is caused to flow into a chamber that includes a material that is configured to alter an appearance of the material based at least in part on a pH level of the dialysate.

In some implementations, dialysate is caused to contact the material.

In some implementations, the material is configured to alter a color of the material based at least in part on the pH level of the dialysate.

In some implementations, the material includes a pH strip.

In some implementations, the material includes a sol-gel.

In some implementations, the pH sensor detects the alteration in the appearance of the material.

In some implementations, one or more artificial light sources are caused to direct light toward the material such that the material reflects at least a portion of the directed light.

In some implementations, the pH sensor is used to detect at least a portion of light reflected by the material.

In some implementations, determining an amount of carbon dioxide includes measuring an amount of $CO_2$ emitted from the dialysate.

In some implementations, determining an amount of carbon dioxide (CO2) in the dialysate includes determining a partial pressure of $CO_2$ associated with a gas emitted by the dialysate.

In some implementations, calculating a net urea in the sample fluid is based at least in part on a difference between the second $CO_2$ gas and the first $CO_2$ gas.

In some implementations, the composition includes an acid.

In some implementations, the acid includes hydrochloric acid.

In some implementations, the composition is heated to a pre-defined temperature.

In some implementations, the second chamber contains a urease.

In some implementations, the second chamber is heated to a desired temperature.

In some implementations, determining the level of total $CO_2$ in the sample fluid includes causing the first $CO_2$ gas to pass between a laser and a receiver configured to detect a beam emitted by the laser.

In some implementations, the beam is emitted at a wavelength that overlaps an absorption spectrum of $CO_2$ gas but does not overlap an absorption spectrum of one or more of NH3 gas, acid gas, and water vapor.

In some implementations, determining the amount of total urea in the fluid includes causing the second $CO_2$ gas to pass between a laser and a receiver configured to detect a beam emitted by the laser.

In some implementations, the beam is emitted at a wavelength that overlaps an absorption spectrum of $CO_2$ gas but does not overlap an absorption spectrum of one or more of NH3 gas, acid gas, and water vapor.

In some implementations, the first portion of the sample fluid or the second portion of the sample fluid is heated in the first or second channel, respectively, to liberate NH3 gas, and determining an amount of NH3 in the sample fluid based at least in part on the NH3 gas.

In some implementations, determining an amount of NH3 in the sample fluid includes causing the NH3 gas to pass between a laser and a receiver configured to detect a beam emitted by the laser.

In some implementations, the beam is emitted at a wavelength that overlaps an absorption spectrum of NH3 gas but does not overlap an absorption spectrum of $CO_2$ gas.

In some implementations, extracting at least one of the first and second portions of fluid from the fluid circuit of the dialysis system includes using a peristaltic pump to extract at least one of the first and second portions of the fluid from a fluid line associated with the fluid circuit.

In some implementations, the first and second portions of fluid include dialysate.

In some implementations, the first and second portions of fluid include blood.

In some implementations, extracting the sample fluid does not interrupt a dialysis treatment session being performed by the dialysis system.

In some implementations, the dialysis system is a hemodialysis system.

In some implementations, the first and second portions of fluid are extracted in a single extraction.

In some implementations, the second chamber contains a urease.

In some implementations, the second chamber is heated to a desired temperature.

In some implementations, the gas emitted from the dialysis fluid delivered to the second chamber is $CO_2$.

In some implementations, the gas emitted from the dialysis fluid delivered to the second chamber is NH3.

In some implementations, the dialysis machine further includes a microprocessor in communication with the pH sensor and the $CO_2$ sensor, the microprocessor being programmed to determine a level of bicarbonate in the dialysis fluid based at least in part on the detected pH and $CO_2$ levels.

In some implementations, the dialysis machine further includes a dialysis fluid inlet line that can be selectively placed in fluid communication with the first chamber or the second chamber, and a pump connected to the dialysis fluid inlet line, the pump being operable to force fluid into the gas emission device via the dialysis fluid inlet line.

In some implementations, the dialysis fluid inlet line is connected to a dialysate line of the dialysis system such that dialysate can be delivered to the gas emission device via the dialysis fluid inlet line.

In some implementations, the dialysis fluid inlet line is connected to a blood line of the dialysis system such that blood can be delivered to the gas emission device via the dialysis fluid inlet line.

Other aspects, features, and advantages will be apparent from the description and drawings, and from the claims.

DETAILED DESCRIPTION

Figure 1:
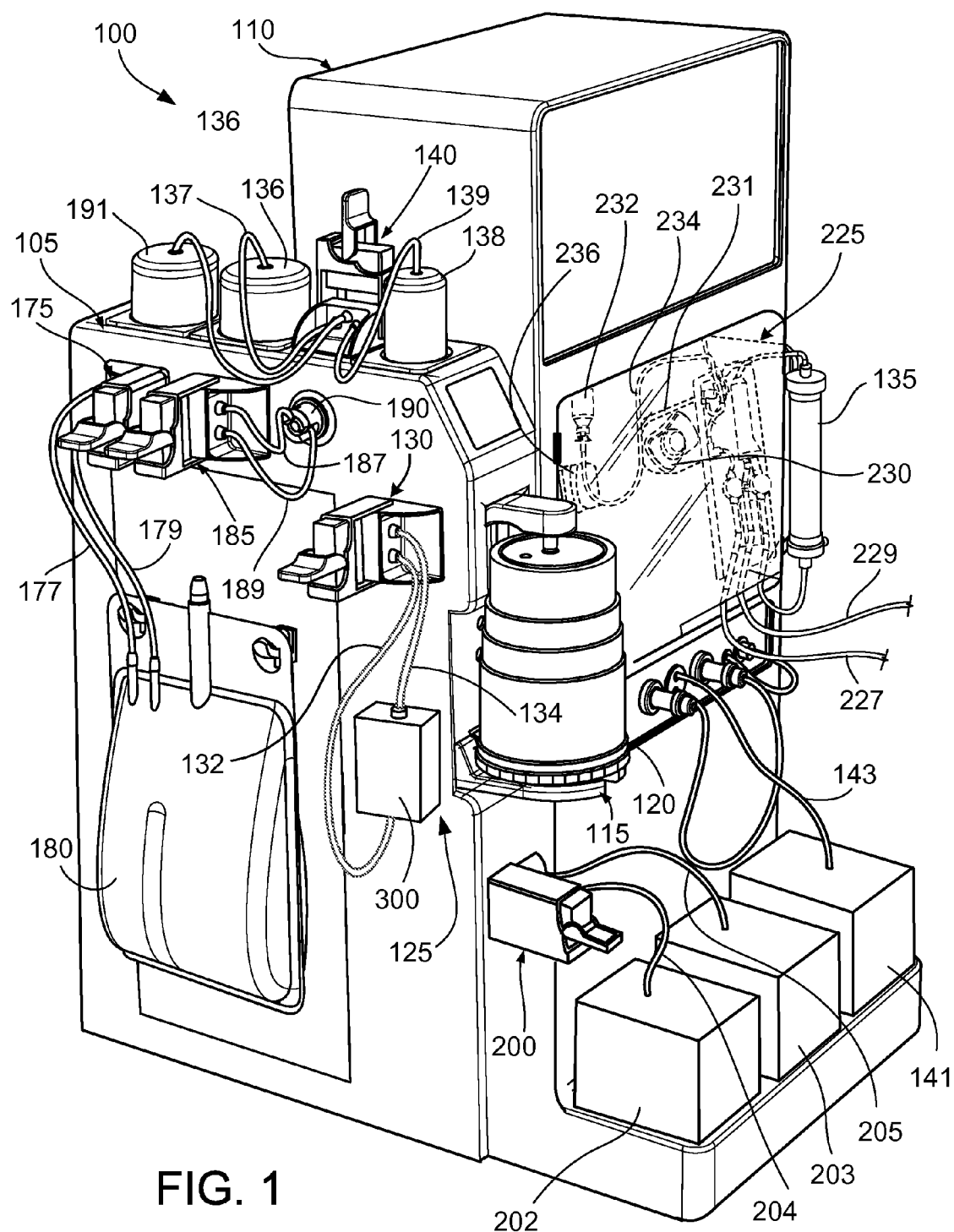
FIG. 1 is a perspective view of a hemodialysis system that includes a hemodialysis machine connected to a module with a sorbent device for recycling spent dialysate.

FIG. 1 shows a hemodialysis system 100 that includes a module 105 fluidly coupled to a hemodialysis machine 110. The module 105 includes, among other things, a sorbent device holder 115 that holds a sorbent device 120. The module also includes a bicarbonate measurement unit 125 that is connected to a manifold 130 of the module 105 via inlet and outlet lines 132, 134. As will be described in greater detail below, the module 105 is used to recycle spent dialysate so that the spent dialysate can be reused for hemodialysis treatment. During use of the hemodialysis system 100, dialysate is pumped from the module 105 to the hemodialysis machine 110. The dialysate is then passed through a dialyzer 135 connected to the hemodialysis machine 110 at the same time that a dialysis patient's blood is passed through the dialyzer 135. As a result, toxins, such as urea, migrate across a permeable membrane (e.g., hollow fibers) of the dialyzer 135 from the patient's blood to the dialysate, producing spent dialysate (i.e., dialysate that contains toxins removed from the patient's blood). The spent dialysate is pumped to the module 105 where it passes through the sorbent device 120, which removes toxins from the spent dialysate. As a result of chemical reactions that occur within the sorbent device 120, the recycled dialysate exiting the sorbent device 120 typically contains gas, such as carbon dioxide. After exiting the sorbent device 120, the recycled dialysate travels into the module 105 and then is drawn into the bicarbonate measurement unit 125 via the inlet line 132, which is connected to the manifold 130 of the module 105. The recycled dialysate is then forced from the bicarbonate measurement unit 125 back into the module 105 via the outlet line 134, which is connected to the manifold 130 of the module 105. The recycled dialysate is then cycled back through the dialysate circuit and reused to cleanse the dialysis patient's blood.

Certain desired substances (e.g., magnesium, calcium, potassium, and sodium) may be stripped from the dialysate as the dialysate passes through the sorbent device 120. Those stripped substances can be added to the dialysate exiting the sorbent device 120 (e.g., prior to drawing the dialysate into the bicarbonate measurement unit 125). As shown in FIG. 1, an infusate solution container 136 and a sodium chloride solution container 138 are connected to a manifold 140 of the module 105 via fluid lines 137 and 139, respectively. The infusate solution (e.g., a solution including magnesium, calcium, and potassium) and sodium chloride can be drawn into the dialysate flowing within the module 105 by activating associated valves and pumps within the module 105. The module 105 may also include a bicarbonate container 191 that is connected to the manifold 140 of the module 104 via fluid line 192. Using a process similar to that discussed above with regard to the infusate solution and the sodium chloride, bicarbonate can be drawn into the dialysate flowing within the module 105 by activating associated valves and pumps within the module 105.

As shown in FIG. 1, a dilution water container 141 is connected to the dialysis machine 110 via a fluid line 143. In some cases, certain substances, such as sodium, may be added to, rather than stripped from, the dialysate as the dialysate passes through the sorbent device 120. As a result, the sodium concentration in the dialysate exiting the sorbent device 120 may exceed a maximum desired concentration. In such cases, dilution water can be added to dialysate that is exiting the hemodialysis machine 110 and flowing into the module 105 toward the sorbent device 120. The dilution water can be added to the dialysate exiting the hemodialysis machine 110 by activating a pump within the hemodialysis machine 110. Activating this pump draws the dilution water from the dilution water container 141 and fluid line 143 into the dialysate exiting the hemodialysis machine 110 such that the sodium concentration of the dialysate exiting the hemodialysis machine 110 (and eventually flowing through the module 105) is reduced, as will be described in greater detail below.

The sodium concentration of the dialysate passing through the dialyzer 135 affects (e.g., increases or decreases) the sodium concentration in the patient's blood. If the sodium concentration in the patient's blood falls outside a desired range, the patient may experience discomfort or illness. For this reason, a conductivity meter may be positioned within the module 105 to measure the conductivity of dialysate after the dialysate exits the sorbent device 120. These conductivity readings can be used during treatment to determine the amount of sodium chloride solution or dilution water to be added to the recycled dialysate exiting the sorbent device 120. In particular, because the sodium in the dialysate is the predominant contributor to the conductivity of the dialysate, the sodium concentration of the dialysate can be determined or approximated based on the conductivity readings. The amount of sodium chloride solution or dilution water to add to the dialysate in order to achieve a desired sodium concentration within the dialysate can then be determined.

In addition to the manifolds 130 and 140, the module 105 includes a manifold 175 to which fluid lines 177, 179 extending from the bag 180 are connected and a manifold 185 to which fluid lines 187, 189 extending from an ammonium (NH4) sensor 190 are connected. The module 105 further includes a manifold 200 by which a fresh dialysate container 202 and a drain container 203 are connected to the module 105 via a fluid line 204 and a drain line 205, respectively. Each of manifolds 130, 140, 175, 185, and 200 can, for example, include projections on which fluid lines can be positioned to connect the various components described above to their respective manifold. Any of various other suitable connection mechanisms can alternatively or additionally be used to connect the fluid lines to the manifolds.

The manifold 175 allows dialysate to be transferred from the module 105 to the bag 180 and vice versa. In particular, using pumps and valves within the module 105, dialysate can be pumped into and suctioned out of the bag 180 via the fluid lines 177, 179 connected to the manifold 175. The manifold 185 permits dialysate to be transferred from the module 105 to the ammonium sensor 190 and vice versa. By activating pumps and valves within the module 105 in a desired manner, the dialysate can be pumped from the module 105 to the ammonium sensor 190 and can be drawn back to the module 105 from the ammonium sensor 190. By activating pumps and valves within the module, fluid can be drawn into the module 105 from the fresh dialysate container 202 via the fluid line 204, and fluid can be pumped from the module 105 to the drain container 203 via the drain line 205. With the sorbent device 120 positioned in the cartridge holder 115, as shown in FIG. 1, fluid circulating within the module 105 is allowed to pass through the sorbent device 120 to recycle the dialysate.

Still referring to FIG. 1, a blood component set 225 is secured to a front face of the hemodialysis machine 110. The blood component set 225 includes arterial and venous patient lines 227, 229 that are connected to a patient during treatment. The arterial patient line 227 is connected to an inlet port of the dialyzer 135 via a series of blood lines, and the venous patient line 229 is connected to an outlet port of the dialyzer 135 via a series of blood lines. A blood pump line 231 positioned between the arterial patient line 227 and the dialyzer 135 is operably connected to a peristaltic blood pump 230 extending from the front face of the hemodialysis machine 110. The peristaltic blood pump 230 can be operated to pump blood through the various blood lines and components of the blood component set 225. In particular, operation of the blood pump 230 draws blood from the patient through the arterial patient line 227. The blood continues through a series of blood lines and blood components (e.g., sensors) to the dialyzer 135. The blood exits the dialyzer 135 and passes through another series of blood lines and components (e.g., sensors) and then is returned to the patient via the venous patient line 229.

As the blood is pumped through the various blood lines and components of the blood component set 225, it may be desirable to inject certain substances, such as drugs and/or saline into the blood lines. As shown in FIG. 1, a drug vial (e.g., a heparin vial) 232 is connected to one of the blood lines via a drug delivery line 234. The drug delivery line 234 is threaded through a peristaltic drug pump 236, which can be used to deliver the drug from the vial 232 to the blood circuit during treatment. A saline bag may also be connected to a blood line of the blood component set 225 via a priming line. This arrangement allows saline to be delivered through the blood circuit formed by the blood lines and components of the blood component set when desired.

In some examples, it is useful to measure an amount of bicarbonate in dialysate while dialysis is being performed on a patient. In some sorbent-based dialysis systems, a bicarbonate concentration of the dialysate is established by the concentration of the fresh dialysate, and by the donation of bicarbonate from the sorbent device 120 (or other sources, such as the bicarbonate container 192) during treatment. The bicarbonate in the premix is circulated through the sorbent device where some of the bicarbonate is broken down due to the acidity of the sorbent device 120. Additional bicarbonate is donated to the dialysate due to the breakdown of a patient's urea in the sorbent device 120. These factors complicate calculating or setting a fixed bicarbonate concentration for the dialysate. Accordingly, it can be useful to measure the bicarbonate concentration of the dialysate during treatment so that a bicarbonate concentration can be maintained during treatment that is appropriate for the patient.

One technique for determining the bicarbonate concentration of a fluid such as dialysate is defined by the Henderson-Hasselbach equation. The Henderson-Hasselbach equation relates the bicarbonate concentration of a fluid with the acidity (pH) of the fluid and the partial pressure of carbon dioxide (CO2) of the fluid. The Henderson-Hasselbach equation is:

$$pH = 6.1 + \log\left(\frac{HCO3}{0.03 * PaCO2}\right)$$

Thus, if two of the constituent concentrations of dialysate can be determined (e.g., the pH level and the partial pressure of CO2), the third concentration (e.g., the bicarbonate concentration) can be calculated based on the known values.

Figure 2:
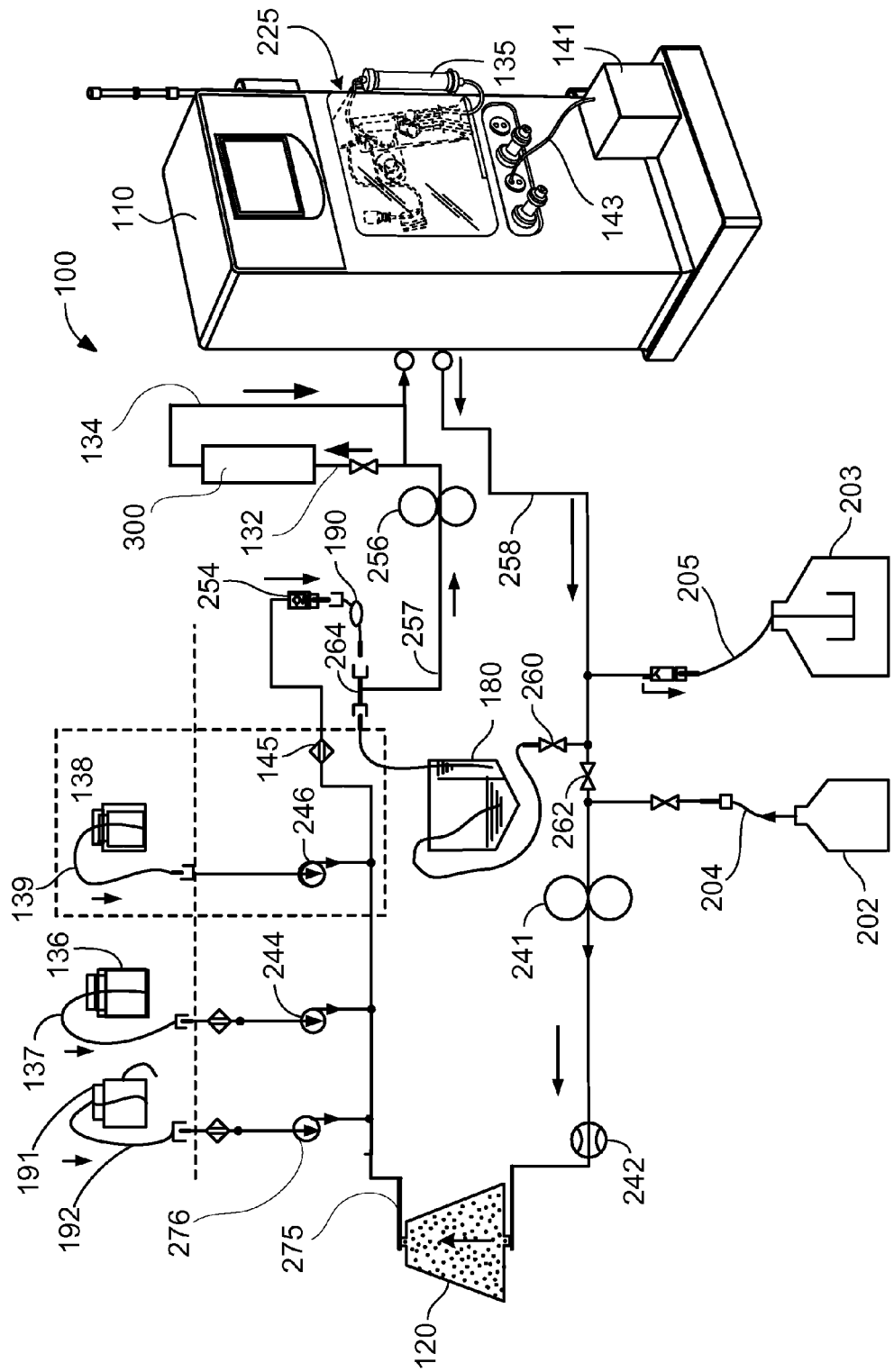
FIG. 2 is a diagram of fluid flow in the dialysis system of FIG. 1.

FIG. 2 schematically illustrates the various components of the module 105 connected to the hemodialysis machine 110. Referring to FIG. 2, a method of performing hemodialysis will now be described. Prior to beginning the dialysis treatment, fresh dialysate is drawn into the module 105 from the fresh dialysate container 202 by selectively activating a pump 241 and various valves of the module 105. The fresh dialysate is then circulated through the module 105 by the pump 241. Prior to reaching the sorbent device 120, the dialysate passes through a flow meter 242 that is configured to measure the flow rate of the dialysate passing therethrough. A signal representing the flow rate of the dialysate can be transmitted from the flow meter 242 to a control unit (e.g., a microprocessor). The control unit can use the detected flow rate of the dialysate to control metering of the infusate solution into the dialysate.

As the dialysate passes through the sorbent device 120, certain substances, such as calcium, magnesium, potassium, and sodium may be stripped from the dialysate. As discussed above, the sorbent device 120 is also adapted to remove toxins, such as urea, from fluid flowing therethrough, but while the fresh dialysate from the fresh dialysate container 202 would generally not contain any such toxins, it would have some capacity to purify dialysate, allowing, for example, tap water to be used as dialysate.

The infusate solution, which includes magnesium, calcium, and potassium, is then pumped into the fluid outlet line 275 from the infusate solution container 136 by activating a pump 244. As discussed above, the infusate solution can be added to the dialysate to restore concentrations of magnesium, calcium, and potassium to desired levels. Maintaining the concentration of these substances within the dialysis solution, such as calcium, magnesium, potassium, and sodium, can help to prevent the patient from experiencing discomfort during and after the treatment.

After introducing the infusate solution into the dialysate, the mixture of the dialysate and infusate solution continues to flow through the fluid outlet line 275 and passes through the conductivity meter 145. The conductivity meter 145 can estimate, based on the conductivity of the dialysate passing therethrough, the concentration of sodium within the dialysate. A pump 246 can then be activated in a manner to introduce sodium chloride solution into the fluid outlet line 275 from the sodium chloride solution container 138 if the conductivity reading indicates that the sodium level in the dialysate is lower than desired. The pump 246 can be operated in a manner to meter a desired volume of sodium chloride solution into the dialysate at a desired rate.

Similarly, a pump internal to the hemodialysis machine 110 can be activated to inject dilution water (e.g., tap water) from the dilution water container 141 into the dialysate exiting the hemodialysis machine 110 and entering the module 105 if the conductivity reading indicates that the sodium level in the dialysate is higher than desired. This dilution water pump can be operated in a manner to meter a desired volume of the dilution water into the dialysate at a desired flow rate.

A microprocessor (which may include the previously mentioned control unit or a different processing device) is connected to the flow meter 242, the conductivity meter 145, and the pumps 241, 244, 246, 256 and 276. The microprocessor is also connected to the dilution water pump inside the hemodialysis machine 110. The measured flow rate of the dialysate is transmitted in the form of a signal from the flow meter 242 to the microprocessor. The microprocessor adjusts operation of the pumps 241 and 256 based on the measured flow rate at the flow meter 242 to ensure that a prescribed dialysate flow rate is achieved. The microprocessor also controls the pump 244 as a function of the flow rate of the dialysate measured by the flow meter 242. This arrangement helps to ensure that a desired amount of the infusate is added to the dialysate, and thus helps to ensure a desired proportion of the infusate to the dialysate.

In response to receiving the signals from the conductivity meter 145, the microprocessor sends signals to the pumps 244 and 246 to cause some of the sodium chloride solution, if desired, to be introduced into the fluid outlet line 275. Similarly, in response to receiving these signals from the conductivity meter 145, the microprocessor can cause the dilution water pump in the hemodialysis machine 110 to pump dilution water, if desired, into the dialysate exiting the hemodialysis machine 110 and entering the module 105. As a result, the amount of sodium chloride and/or dilution water delivered to the dialysate can better achieve a desired sodium concentration within the dialysate (e.g., a sodium concentration that closely matches the sodium concentration prescribed by the dialysis patient's physician).

After passing through the conductivity meter 145, the dialysate passes through a check valve 254 and into the ammonium sensor 190, which detects ammonium levels within the dialysate.

After filling the bag 180 to a desired level with dialysate having a desired concentration of calcium, magnesium, potassium, and sodium, a pump 256 is activated to draw the dialysate from the bag 180 into the hemodialysis machine 110 via fluid line 257. Before entering the hemodialysis machine 110, the dialysate may be caused to flow (e.g., upon the activation of one or more valves) into the dialysate collection unit 300 via the inlet line 132. The amount of bicarbonate in the dialysate is measured by the bicarbonate measurement unit 125 while the dialysate flows through the dialysate collection unit 300 (e.g., using the techniques described below), and is returned to the fluid line 257 via the outline line 134.

Based on the amount of bicarbonate measured in the dialysate by the bicarbonate measurement unit 125, bicarbonate can be added to the dialysate from the bicarbonate container 191. For example, a pump 276 can be activated which draws bicarbonate into the fluid line 275 via a bicarbonate fluid line 192 from the bicarbonate container 191. Drawing bicarbonate into the fluid line 275 will alter the bicarbonate level of the dialysate, and can be continuously measured by the bicarbonate measurement unit 125 and adjusted until the desired level of bicarbonate is reached (e.g., a level of bicarbonate that is appropriate for a patient).

The dialysate is circulated through the hemodialysis machine 110 and passes through the dialyzer 135 connected to the hemodialysis machine 110. At the same time, a patient's blood is circulated through the blood component set 225, including the dialyzer 135, connected to the hemodialysis machine 110. As a result, toxins, such as urea, are transferred across a permeable membrane (e.g., permeable microtubes) of the dialyzer 135 from the patient's blood to the dialysate. The spent dialysate exiting the dialyzer 135 is then routed back to the module 105.

The spent dialysate passes through a fluid line 258 in the module 105. Depending on the desired volume of dialysate to be cycled back to the dialysis machine, some of the spent dialysate can be routed to a spent dialysate chamber of the bag 180 via open valve 260 while the remainder of spent dialysate is routed toward the sorbent device via open valve 262. As a result of the dialysis, for example, fluid from the patient may be added to the dialysate as the dialysate passes through the dialyzer 135. Thus, routing some of the spent dialysate to the bag 180 can help to ensure that a substantially constant volume of dialysate is circulated through the module 105 and/or the hemodialysis machine 110 throughout treatment. The pump 241 along the fluid line 258 forces the volume of the spent dialysate that is not routed to the bag 180 into the sorbent device 120 via the cartridge holder 115. As the spent dialysate passes through the sorbent device 120, urea is removed from the spent dialysate. Calcium, magnesium, and potassium are also stripped from the spent dialysate by the sorbent device 120.

In the manner discussed above, after the recycled dialysate exits the sorbent device 120, the infusate solution is introduced into the recycled dialysate and, based on the conductivity reading at the conductivity meter 145, sodium chloride may be added to the recycled dialysate. Similarly, dilution water can be added to the spent dialysate exiting the hemodialysis machine 110 and entering the module 105 based on the reading at the conductivity meter 145. In the initial stages of treatment, sodium levels in the recycled dialysate tend to be lower than desired due to the tendency of the sorbent device 120 to strip sodium from the dialysate passing therethrough. Consequently, in the early stages of the treatment, sodium chloride will typically be injected into a fluid line to increase the concentration of sodium in the recycled dialysate. In later stages of the treatment, however, the sorbent device 120 may contain high levels of sodium and thus release sodium into the spent dialysate as the spent dialysate passes through the sorbent device 120. This can lead to higher than desired levels of sodium in the recycled dialysate passing through the fluid outlet line 134. In such cases, dilution water is injected into the spent dialysate exiting the hemodialysis machine 110 and entering the module 105 to lower the sodium concentration of the spent dialysate. This spent dialysate then travels through the module 105 to the sorbent device 120 where the dilution water and spent dialysate are filtered.

Injecting the dilution water into the spent dialysate before the spent dialysate passes through the sorbent device 120 to be filtered allows the use of tap water as the dilution water because the tap water will be filtered and purified as it passes through the sorbent device 120. This arrangement permits the hemodialysis system 100 to be operated with a readily available supply of dilution water and without the need for storing large volumes of dilution water on site.

After flowing past the conductivity meter 145, the recycled dialysate passes through the check valve 254 and into the ammonium sensor 190. After exiting the ammonium sensor 190, some of the recycled dialysate is routed to the bag 180 and some of the recycled dialysate is routed to the hemodialysis machine 110. The dialysate may again enter the bicarbonate measurement unit 125 via the inlet line 132 and a valve if further monitoring of the dialysate's bicarbonate level is desired. The measurements provided by the bicarbonate measurement unit 125 can be used to further alter the bicarbonate level of the dialysate (e.g., by introducing additional bicarbonate from the bicarbonate container 191 into the dialysate).

In order to ensure that an equal amount of fluid enters and exits the hemodialysis machine 110, a T-valve 264 is adapted to route a portion of the dialysate to the hemodialysis machine 110 via the fluid line 257 and to route excess dialysate to the fresh dialysate chamber of the bag 180. Because the flow rate of the dialysate at the T-valve 264 is generally greater than the rate at which the dialysate is being pulled into the hemodialysis machine 110, there will typically be excess dialysate passing through the T-valve 264 and that excess dialysate will be routed to the bag 180 where it is collected for later use.

The dialysate that is delivered to the hemodialysis machine 110 again passes through the dialyzer where toxins are transferred from the patient's blood to the dialysate. The spent dialysate is then routed back to the module and the process is repeated until a desired amount of toxins has been removed from the patient's blood.

After completing the patient's treatment, the dialysate can be removed from the bag 180. For example, the pumps and valves of the module 105 can be operated in a manner to pump the dialysate from the bag 180 into the drain container 203 or into a plumbing drain. Emptying the bag 180 can allow the user to more easily handle the bag 180 after treatment due to the decreased weight.

After draining the bag 180 to a desired level, the external components (e.g., the sorbent device 120, the infusate container 136, the bicarbonate measurement device 125, the sodium chloride container 138, the bicarbonate container 192, the bag 180, the dialysate container 202, the drain container 203, and their associated fluid lines), which are constructed as disposable, single use components, are disconnected from the module 105 and discarded.

Figure 3:
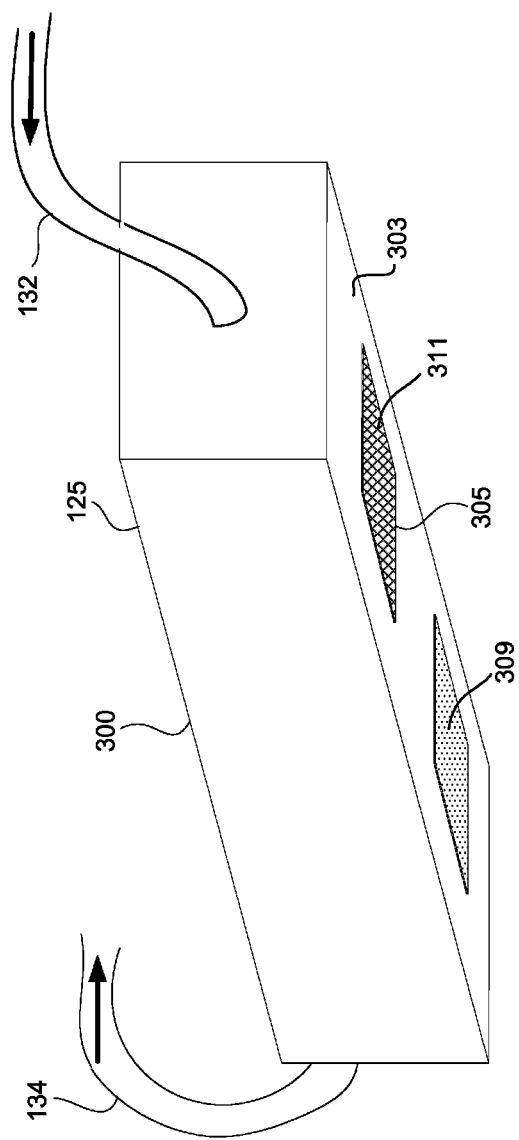
FIG. 3 is a diagram of an apparatus of the dialysis system of FIG. 1 that is used in measuring bicarbonate.

Referring to FIG. 3, a dialysate collection unit 300 of the bicarbonate measurement unit 125 is shown that, when used in combination with one or more sensors of the bicarbonate measurement unit 125, can measure the pH and the partial pressure of $CO_2$ of dialysate. In some examples, the dialysate collection unit 300 is a disposable component that can be removably attached to the bicarbonate measurement unit 125. After the pH and the partial pressure of $CO_2$ of the dialysate have been determined, the Henderson-Hasselbach equation can be used to calculate a bicarbonate concentration of dialysate as shown above.

The dialysate collection unit 300 includes a main body that is in fluid communication with the inlet line 132 that carries dialysate. In general, the main body of the dialysate collection unit 300 defines a chamber which is adapted to receive dialysate from the inlet line 132. The main body is also in fluid communication with the outlet line 134 that routes the dialysate back into the module 105. The inlet line 132 and the outlet line 134 may be detachably connected to the dialysate collection unit 300. In some examples, the main body is a cuvette (e.g., a tube of circular or square cross section, made of plastic, glass, or fused quartz, that is designed to hold samples, especially for spectroscopic experiments).

A surface 303 of the main body of the dialysate collection unit 300 defines an opening 305. The opening 305 is covered by a gas-permeable membrane 311, such that dialysate flowing through the dialysate collection unit 300 will flow over (but not through) both the opening 305 and the gas-permeable membrane 311. In some examples, the gas-permeable membrane 311 is a breathable, waterproof fabric, such as Gor-Tex®. The main body of the dialysate collection unit 300 also includes one or more surfaces (e.g., surface 303) to which a pH-reactive material 309 has been applied in such a way that dialysate flowing through the dialysate collection unit 300 will contact the pH-reactive material 309. As described in further detail below, when the pH-reactive material 309 and the gas-permeable membrane 311 are aligned with appropriate sensors (e.g., sensors located on the module 105), the bicarbonate measurement unit 125 can be used to measure the amount of bicarbonate in dialysate flowing through the main body of the dialysate collection unit 300 without contacting the liquid dialysate with sensors or probes.

The main body of the dialysate collection unit 300 is configured to receive a flow of dialysate via the inlet line 132 and may partially or completely fill with dialysate. With dialysate flowing on one side of the gas-permeable membrane, gas emitted from the dialysate will pass through the gas-permeable membrane 311, and can be detected and analyzed by one or more sensors as described below. Thus, dialysate flows into the dialysate collection unit 300 via inlet line 132 and fills at least a portion of the main body and exits the main body via the outlet line 134. While the dialysate is in the main body of the dialysate collection unit 300, the pH-reactive material 309 and the gas-permeable membrane 311 can be used to determine the pH level and the partial pressure of $CO_2$ of the dialysate, respectively. Examples of techniques and devices used to calculate the pH level and partial pressure of $CO_2$ of the dialysate using, for example, the arrangement of FIG. 4 is discussed below.

Figure 4:
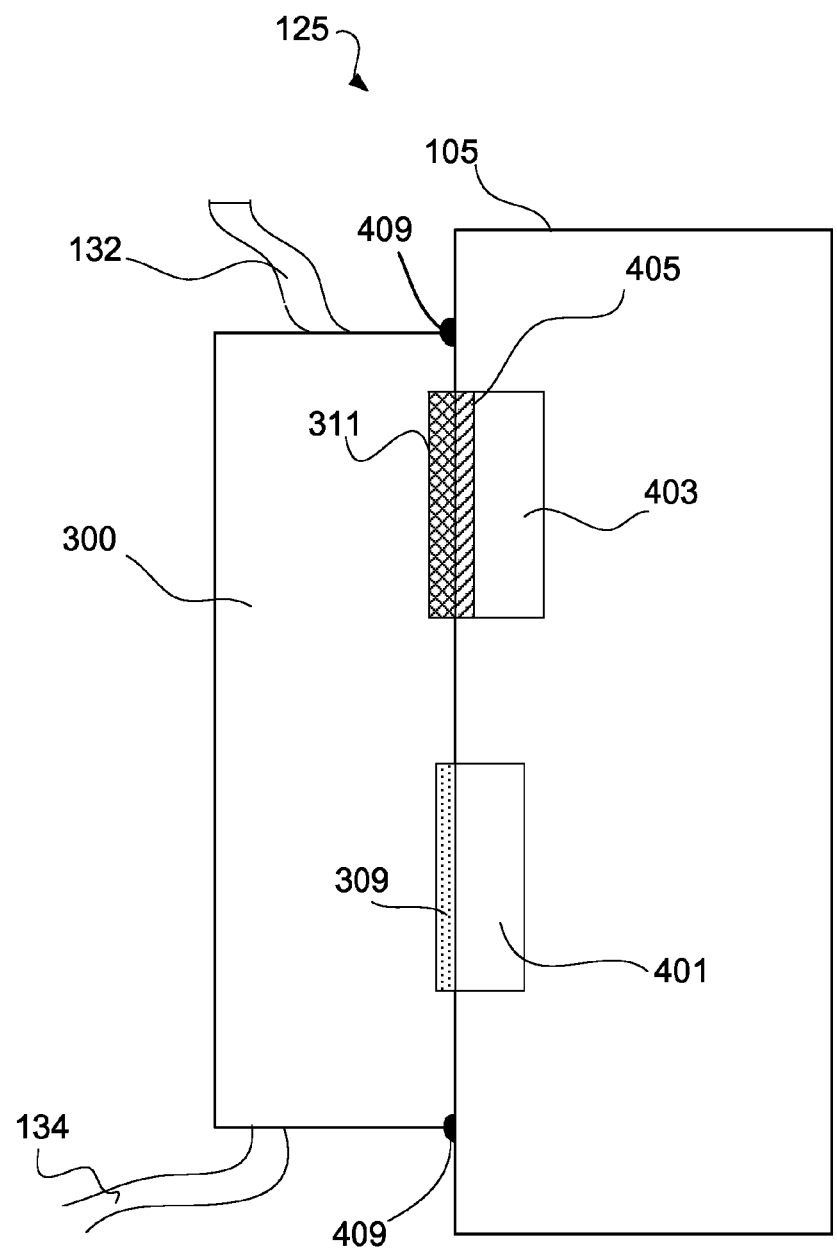
FIG. 4 is a diagram of the apparatus of FIG. 3 connected to the hemodialysis machine.

FIG. 4 is a perspective view of the bicarbonate measurement unit 125 as used in the system of FIG. 1. In the example of FIG. 4, the dialysate collection unit 300 is coupled to the module 105 via a coupling mechanism 409 that contacts one or more surfaces of the dialysate collection unit 300 and the module 105. Examples of the coupling mechanism 409 include one or more snaps, latches, adhesives, hook and loop fasteners, magnets, and the like. The dialysate collection unit 300 is coupled to the module 105 such that the gas-permeable membrane 311 and the pH-reactive material 309 are aligned with a $CO_2$ sensor and a pH sensor, respectively. In the example of FIG. 4, the $CO_2$ sensor 403 is an infrared gas sensor.

As described above, when dialysate flows through the main body of the dialysate collection unit 300, gas emitted from the dialysate is transferred through the gas-permeable membrane 311. The gas emitted from the dialysate is transferred into a gas collection chamber 405 of the $CO_2$ sensor 403, and may include both $CO_2$ gas as well as other gases. After the gas has passed through the gas-permeable membrane 311 and has entered the gas collection chamber associated with the $CO_2$ sensor 403, the $CO_2$ sensor 403 can measure the concentration of $CO_2$ gas present in the gas collected in the gas collection chamber 405. In some examples, the gas collection chamber forms a seal with the gas-permeable membrane 311 and/or a surface of the dialysate collection unit 300 such that most or all of the gas that has permeated the gas-permeable membrane 311 passes directly into the gas collection chamber 405 of the $CO_2$ sensor 403.

In some examples, the $CO_2$ sensor 403 is an infrared gas sensor configured to detect an amount of $CO_2$ in a fluid, such as the gas collected in gas collection chamber 405. The $CO_2$ sensor 403 may include an infrared source (e.g., a lamp or laser), a wavelength filter, and an infrared detector. When the $CO_2$ gas enters the $CO_2$ measurement chamber, the gas concentration can be measured electro-optically by the gas's absorption of a specific wavelength in the infrared (IR). The IR light is directed through the gas collection chamber 405 a detector associated with the $CO_2$ sensor. The IR light can also be reflected back toward a detector; that is, the detector does not necessarily need to be positioned opposite the IR source. The detector may include an optical filter that eliminates all light except the wavelength that the selected gas molecules can absorb, which allows the detector to measure the absorption of the characteristic wavelength of light absorbed by the $CO_2$ gas in the gas collection chamber 405. The $CO_2$ sensor 403 can then use the collected information to determine the concentration of $CO_2$ in the gas collection chamber 405. The IR signal from the IR source can be chopped or modulated so that thermal background signals can be offset from the desired signal.

According to Henry's law, the partial pressure of free $CO_2$ in a gas in equilibrium with (e.g., above) the dialysate is proportional to the dissolved $CO_2$ in the dialysate. That is, Henry's law describes the equilibrium between a vapor and a liquid. At a constant temperature, Henry's law states:

$$p = k_H c,$$

where p is the partial pressure of the solute in the gas in equilibrium with the solution, c is the concentration of the solute and $k_H$ is a constant with the dimensions of pressure divided by concentration. The constant, known as the Henry's law constant, depends on the solute, the solvent and the temperature. The relationship between the solubility of $CO_2$ and temperature is shown below.

| | Temperature (° C.) | | | | | | | |
|---|---|---|---|---|---|---|---|---|
| | 0 | 10 | 20 | 30 | 40 | 50 | 80 | 100 |
| Solubility (cm3 $CO_2$/g water) | 1.8 | 1.3 | 0.88 | 0.65 | 0.52 | 0.43 | 0.29 | 0.26 |

Thus, using Henry's law in combination with the measured concentration of $CO_2$ gas in equilibrium with the dialysate, the concentration of dissolved $CO_2$ in the dialysate can be determined.

Figure 5:
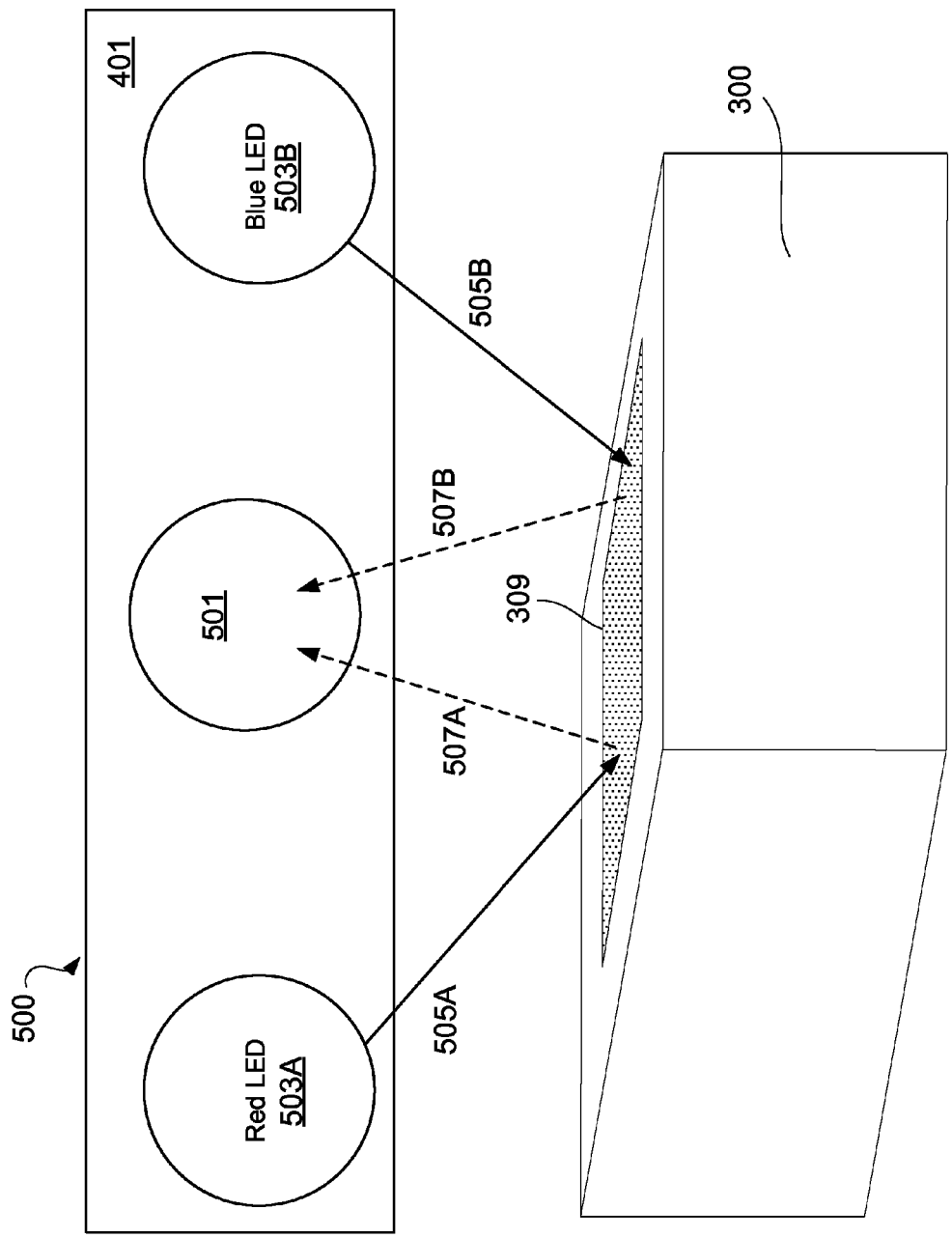
FIG. 5 is a diagram of an apparatus for measuring a pH level of dialysate.

As shown by the Henderson-Hasselbach equation above, once the $CO_2$ of the dialysate has been determined, calculating the pH of the dialysate will yield the values that are necessary to calculate the bicarbonate concentration of the dialysate. FIG. 5 represents an exemplary technique for determining a pH level of the dialysate.

The dialysate collection unit 300 is coupled to the module 105 such that the pH reactive material 309 is aligned with the pH sensor 401. As described above, when dialysate flows through the main body, the dialysate contacts and reacts with the pH reactive material 309 which can be a pH indicator strip. In general, a pH indicator strip is a material that changes color depending on the pH—the acidity or alkalinity—of a liquid. pH indicators are sometimes weak acids or weak bases that change color at specific pHs. For instance, methyl red is a common indicator that is red at pH of 5 and yellow at a pH of 6. Indicators which are covalently bonded to the strip substrate can be used when using indicator strips to avoid contamination of the dialysate. In some examples, the pH reactive material 503 can be a sol-gel that is applied to one or more inner surfaces of the pH measurement chamber 309. The sol-gel can be of a type that reacts with the dialysate to change color in a manner similar to that of a pH indicator strip.

In some examples, the pH reactive material 309 is coupled to an inner, clear surface of the main body of the dialysate collection unit 300 (e.g., a surface opposite the pH sensor 401, as shown in FIG. 4). When the dialysate contacts the pH reactive material 309 for a sufficient length of time, the pH reactive material 309 will change its color to a color that represents the acidity or alkalinity of the dialysate. The pH sensor 401 is configured to detect the color state of the pH reactive material 309 and determine the acidity or alkalinity of the dialysate based on the detected color state. An exemplary technique for using a pH sensor 401 in combination with a pH reactive material 309 to determine the acidity or alkalinity of the dialysate is shown in FIG. 6 (discussed below).

FIG. 5 shows an example arrangement 500 for determining the pH level of dialysate flowing through the main body of the dialysate collection unit 300. The arrangement 500 includes the pH sensor 401, which includes a phototransistor 501, and red and blue LEDs 503A, 503B. The phototransistor 501 is aligned with the main body of the dialysate collection unit 300 to detect light reflected from the pH reactive material 309. Light from either the red LED 503A or the blue LED 503B is emitted toward the pH reactive material 309 through a clear surface of the main body such that the emitted light reflects off the pH reactive material 309. In some examples, the pH reactive material 309 has a "fuzzy" or "matte" surface such that light may be reflected regardless of the angle. In some examples, the dialysate collection unit 300 is positioned at an acute angle (e.g., 20 degrees) with respect to the phototransistor 501 to avoid reflecting light from a surface of the main body back onto the phototransistor 501.

Figure 6:
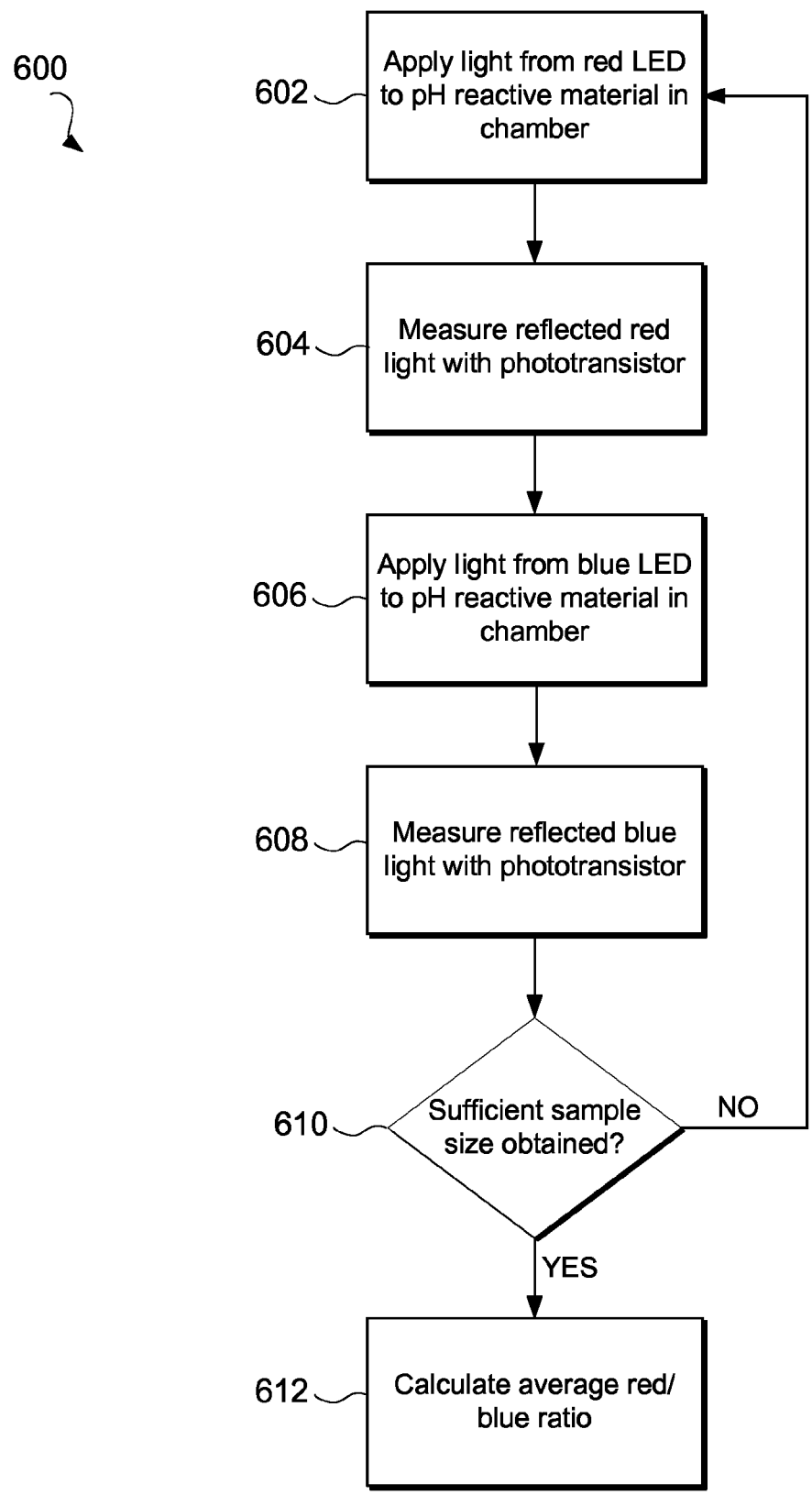
FIG. 6 illustrates a technique for determining a pH level of dialysate.

FIG. 6 illustrates an example process 600 for using the pH sensing arrangement 500 to determine the pH of the dialysate. Referring to both FIGS. 5 and 6, the process 600 begins when the red LED 503A emits red light 505A toward the pH reactive material 309 (602). The phototransistor 501 captures the light 507A reflected from the pH reactive material 309 (604). The blue LED 503B emits blue light 505B toward the pH reactive material 309 (606). The phototransistor 501 captures the light 507B reflected from the pH reactive material 309 (608). A processor associated with the pH sensor 401 (e.g., the main processor of the hemodialysis system 100) determines whether a sufficient sample size has been obtained (610). If a sufficient sample size has not been obtained (NO), the process 600 begins applying light and capturing reflected light in the sequence described above. If a sufficient sample size has been obtained (YES), the processor calculates the average red/blue ratio (e.g., the average amount of red light and blue light reflected by the pH reactive material 309). The amount of blue or red light detected by the phototransistor 501 can be represented by the difference between an output value of the phototransistor 501 when an LED is emitting light, and an output value of the phototransistor 501 when no LEDs are emitting light. It should be noted that the process 600 need not follow the exact sequence described above. For example, the blue LED 503B may emit blue light 505B before the red LED 503A emits red light 505A. The average blue/red ratio can then be used to determine pH via an empirically determined nonlinear curve fit. If desired, lots of pH reactive material may be tested and calibrated, with calibration data included in the disposable. The calibration data may be read by any suitable means including barcode, serial ROM or RFID.

Figure 7:
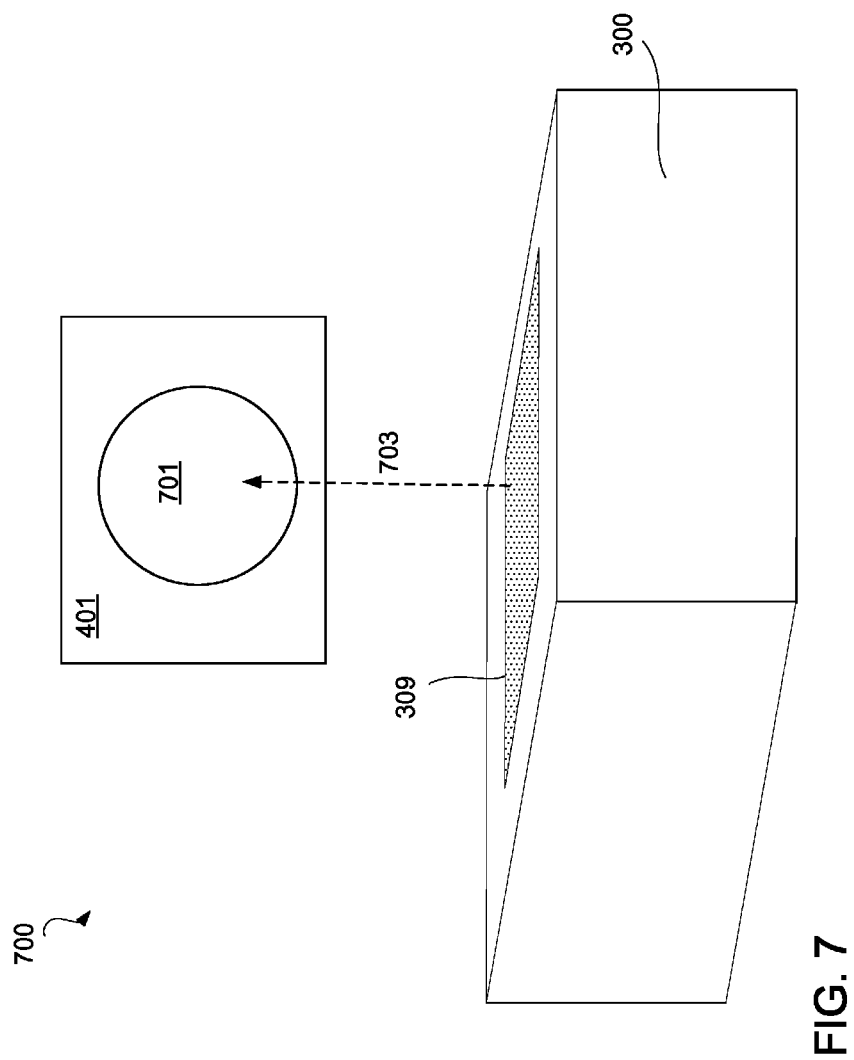
FIG. 7 is a diagram of an apparatus for measuring a pH level of dialysate.

FIG. 7 is an example pH sensing arrangement 700 for determining the pH of dialysate in contact with the pH reactive material 309. In this example, the pH sensor 401 includes a camera 701 aligned with the pH reactive material 309. When the pH reactive material 309 is contacted by the dialysate and changes color, the camera 701 (e.g., a color camera) can optically capture the color state of the pH reactive material 309. Software, hardware, or a combination thereof associated with one or more of the hemodialysis machine or the camera may then use the captured color information to determine the pH level of the dialysate.

Figure 8:
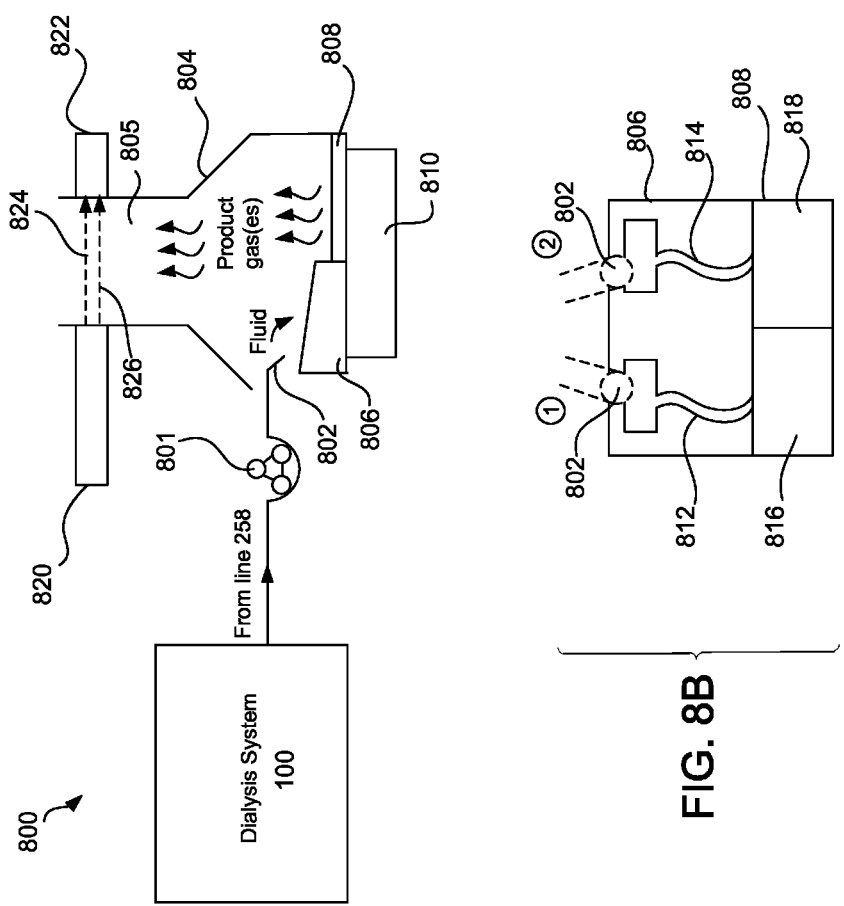
FIGS. 8A and 8B show side and top views, respectively, of a chemical measurement system for use with dialysis machines.

In some examples, it is also possible to measure bicarbonate levels or other chemical properties of a sample fluid (e.g., blood or dialysate) using other related techniques. FIGS. 8A and 8B show top and side views of a chemical measurement system 800 for use with dialysis machines. Briefly, by subjecting a sample fluid such as dialysate to one or more conditions, chemical properties can be determined for one or more of the sample fluid and a second associated fluid (e.g., the blood of a patient who is undergoing treatment).

In FIG. 8A, a sample of dialysate is extracted from a fluid path in the dialysis system. For example, a peristaltic (or "roller") pump can be used to extract dialysate from the fluid line 258 (FIG. 2), near an outlet of the dialyzer. After being extracted from the fluid circuit in the dialysis system 100, the sample fluid can be drawn through a fluid line 802 into a measurement system 804. The fluid line 802 is arranged to deposit the sample fluid onto a heater block 806. For example, the fluid line 802 could be positioned above the heater block 806 so that sample fluid exiting the fluid line 802 falls onto the heater block 806. The heater block 806 can be positioned on top of a loadcell 810 to measure a precise quantity of sample fluid that has been transferred to the measurement system 804 (e.g., by measuring the weight of the sample fluid). Additionally, the heater block could have a defined volume wherein overflow is discarded. The amount of sample fluid detected by the load cell 810 can be compared with a displacement of the pump 801 to provide safety redundancy.

Once the sample fluid has been drawn into the measurement system 804, the sample fluid can be subjected to a number of conditions in order to identify one or more chemical properties of the sample fluid. For example, as described below, the measurement system 804 can be used to determine the blood urea nitrogen ("BUN"), ammonia ($NH_3$), and total carbon dioxide ($CO_2$, as a sum of $pCO_2$ and bicarbonate) levels of the sample fluid. By liberating certain gases from the sample fluid using one or more conditions such as heat, chemical compounds, changes in pressure, or a combination thereof, an optical detection system that includes a laser 820 and an optical detector 822 can be used to identify properties of the sample fluid based on the liberated gases that rise into beams emitted by the laser 820. Other light sources and optical filters may be used in place of a laser.

As shown in FIG. 8B, the heater block 806 can include a first heated channel 812 and a second heated channel 814. The fluid line 802 can be movably positioned over either the first heated channel 812 (in position "1") or the second heated channel 814 (in position "2") such that sample fluid exiting the fluid line 802 will fall into one of the heated channels 812, 814. In either position, the sample fluid can be heated as it travels down the heated channel (e.g., to approximately 95° C.) in order to drive off $NH_3$ and some $CO_2$ from the sample fluid. Because the vapor pressure of ammonia is higher than that of water, heating the sample fluid in such a manner can drive off ammonia, liberating $NH_4+$ as $NH_3$ gas. The $NH_3$ gas, once liberated, travels up the chimney 805 into the path of one or more beams 824, 826 emitted by the laser 820. The detector 822 can determine properties of the gas passing through a beam (e.g., beam 824) based on the light that passes through the gas. The wavelength of the beams 824, 826 is based on absorption properties of the gases that are desired to be measured or excluded from measurement. Accordingly, if the beam 824 is emitted at a wavelength (e.g., 1.52 μm) that ignores the absorption factors of water vapor and/or other gases (e.g., $CO_2$ gas) and overlaps with an absorption range of $NH_3$, the amount of the beam 824 absorbed by the gas can be detected and measured by the detector 822 in order to determine the properties of the gas (e.g., a concentration of $NH_3$ in the gas). This process allows the measurement system 804 to determine the amount of blood ammonia in the sample fluid.

If the sample fluid is dialysate, the amount of ammonia in the blood of a patient undergoing dialysis can be determined based on the amount of ammonia in the dialysate.

The measurement system 804 can also be used to measure the total $CO_2$ of the sample fluid, where the total $CO_2$ represents the sum of $pCO_2$ and bicarbonate. In some examples, the fluid line 802 is arranged in position "1" and deposits sample fluid into the heated channel 812. The sample fluid travels down the heated channel 812 (which is formed in a declined surface of the heater block 806) and is deposited in a first chamber 816 of a container unit 808 that includes the first chamber 816 and a second chamber 818. In some examples, the container unit 808 can be a disposable unit that is discarded after a predetermined number of uses or after a predetermined time of service. The first chamber 816 contains an acid (e.g., diluted HCL) that has been heated to a predetermined temperature depending upon the desired reaction rate (e.g., 70 C). Solid acids may also be used with the advantage of not evaporating during the course of the treatment. Metal bicarbonates (e.g., NaHCO3) are decomposed by acid (e.g. $NaHCO_3+HCL \rightarrow NaCl+H_2CO_3$, $H_2CO_3 \rightarrow CO_2+H_2O$), so depositing the sample fluid in the acid in the first chamber 816 will liberate CO2 gas associated with the decomposition of bicarbonates such as $HCO_3-$. Furthermore, because the vapor pressure of $CO_2$ is higher than that of water, depositing the sample fluid in acid at a sufficiently high temperature will liberate substantially all of the dissolved CO2 from the sample fluid. Thus, the total $CO_2$ ($pCO_2$+bicarbonate) of the sample fluid can be determined by measuring the total $CO_2$ emitted from the sample fluid deposited into the first chamber 816.

The liberated $CO_2$ gas travels up the chimney 805 into the path of the beam 826 emitted by the laser 820. The beam 826 is emitted at a wavelength (e.g., 2.10 μm) that overlaps an absorption spectrum of $CO_2$ gas but does not overlap the absorption spectrums of one or more of $NH_3$ gas, acid gas, and water vapor. Accordingly, in a manner similar to that discussed above, the detector 822 can determine the level of $CO_2$ in the gas emitted from the sample fluid that was deposited into the first chamber 816. The level of bicarbonate or $pCO_2$ associated with the sample fluid can also be determined by calculation. For example, the $CO_2$ concentration detected may be integrated over the detection time to give total $CO_2$ emission in moles, giving moles of $NaHCO_3$ (1:1). The $NaHCO_3$ concentration may be computed from a known weight or volume of fluid; however, other salts may also contribute $CO_2$.

The measurement system 804 can also be used to measure the level or urea in the sample fluid. In some examples, the fluid line 802 is arranged in position "2" and deposits sample fluid into the heated channel 814. The sample fluid travels down the heated channel 814 (which is formed in a declined surface of the heater block 806) and is deposited in the second chamber 818 of the container unit 808. This container includes conditions that can liberate gases associated with the urea content of the sample fluid. For example, the second chamber 818 can contain a urease (e.g., jack bean meal urease) that decomposes the urea in the sample fluid, resulting in $CO_2$ and $NH_3$ reaction product gases. Either the $CO_2$ or the $NH_3$ reaction product gases can be measured using the laser 820 and the detector 822 to provide the level of urea in the sample fluid. Depending which reaction product gas is selected to be used as an indication of the urea in the sample fluid, a laser that has a wavelength overlapping an absorption factor of the selected reaction product gas is used to detect the properties of the gases emitted from the sample fluid.

Figure 9:
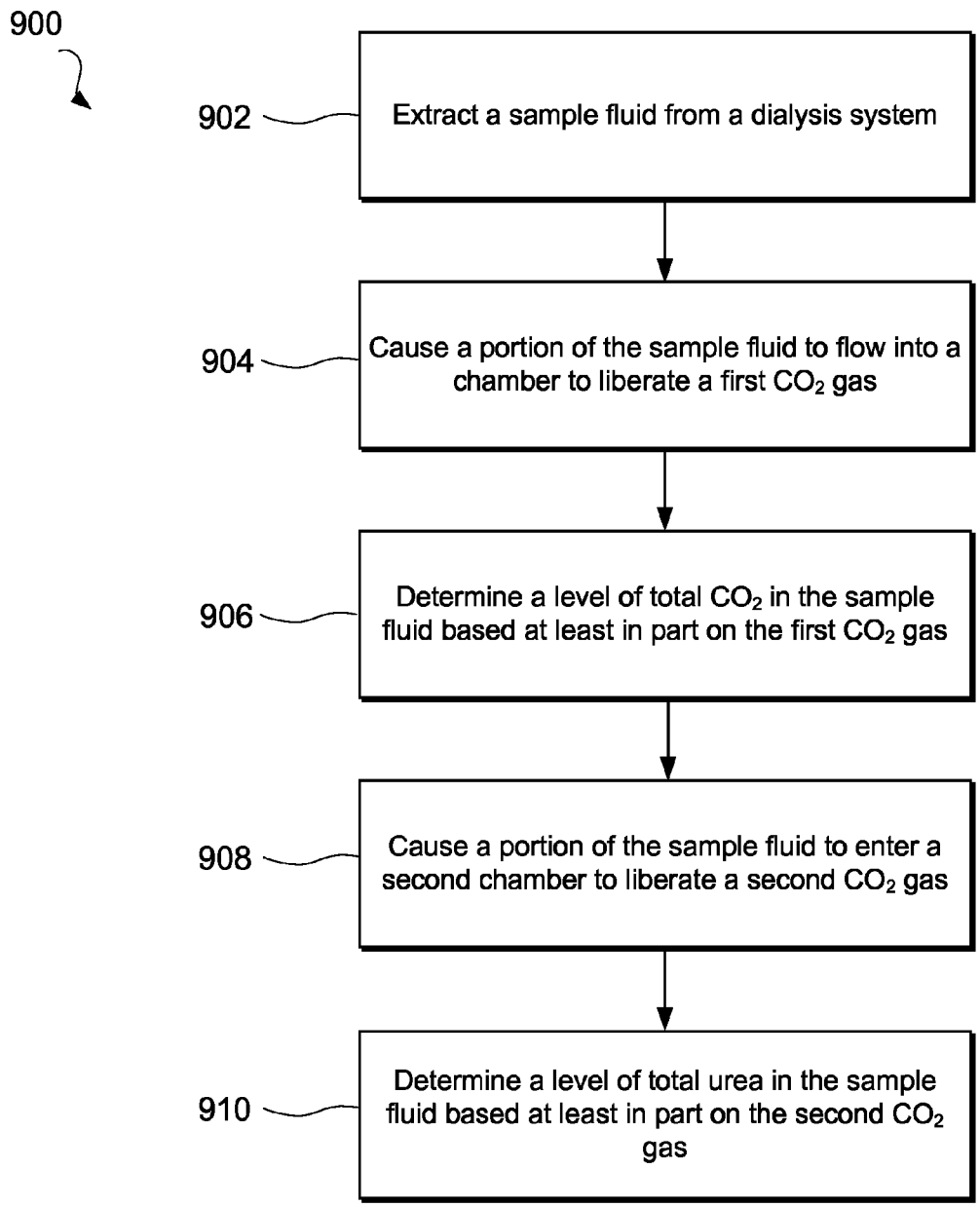
FIG. 9 illustrates a process for measuring the chemical properties of a sample fluid.

FIG. 9 illustrates a process 900 for measuring the chemical properties of a sample fluid, such as dialysate or blood. A fluid sample is extracted from a dialysis system (902). In some examples, the fluid can be extracted from the dialysis system without interrupting a patient's ongoing treatment session. The fluid can be extracted using a variety of techniques and systems, such as the roller pump arrangement illustrated in FIG. 8A. The amount of sample fluid extracted can be controlled at the point of extraction, and the actual amount of sample fluid extracted for measurement can be confirmed (e.g., using the loadcell 810 shown in FIG. 8A).

A portion of the sample fluid is caused to flow into a chamber to liberate a first $CO_2$ gas (904). For example, as shown in FIGS. 8A and 8B, the sample fluid (or a portion thereof) may be deposited in a heated channel that leads to a first chamber at the base of an inclined surface. The sample fluid can be heated to liberate one or more gases while the sample fluid travels toward the first chamber. In some examples, these gases (e.g., $NH_3$) can be used to measure an amount of ammonia in the sample fluid. The first chamber contains conditions that liberate $CO_2$ gas from the sample fluid. For example, the first chamber may contain a heated acid (e.g., diluted HCl) that liberates both water vapor and $CO_2$ from the sample fluid. The amount of urease provided in the first chamber should be sufficient to resist contaminates for the duration of the desired testing period (e.g., one chemical level test, one dialysis treatment session, or longer). The liberated gases can drift upward toward a measurement point (e.g., the liberated gases can drift up a chimney such that they pass through one or more laser beams that traverse an opening of the chimney).

A level of total $CO_2$ in the sample fluid is determined based at least in part on the first $CO_2$ gas (906). For example, using the laser detection arrangement shown in FIG. 8A, a measurement system (e.g., measurement system 804) can determine the total level of $CO_2$ in the sample fluid. The total level of $CO_2$ represents a sum of $pCO_2$ and bicarbonate in the sample fluid.

A portion of the sample fluid is caused to enter a second chamber to liberate a second $CO_2$ gas (908). For example, the fluid line 802 can be actuated to a second position in order to deposit a second portion of the sample fluid (or all of the sample fluid) into a second heated channel that leads to a second chamber, or both chambers may be on a movable stage. The sample fluid can be heated to liberate one or more gases while the sample fluid travels toward the second chamber. The second chamber includes conditions to liberate gases from the sample fluid. For example, the second chamber can include a urease (e.g., jack bean meal urease) that decomposes urea to liberate a product $CO_2$ gas. The amount of reactant provided in the second chamber should be sufficient to resist contaminates for the duration of the desired testing period (e.g., one chemical level test, one dialysis treatment session, or longer). The second chamber may contain other conditions, such as heat and/or pressure, which may also interact with the sample fluid to liberate a product gas. The liberated gases can drift upward toward a measurement point (e.g., the liberated gases can drift up a chimney such that they pass through one or more laser beams that traverse an opening of the chimney). While $CO_2$ is used in this example as the product gas that will be measured, other gases could also be selected to serve as an indicator of the amount of urea in the sample fluid. For example, $NH_3$ can also be liberated in the second chamber using jack bean meal urease and can be measured to determine the amount of urea in the sample fluid.

A level of total urea in the sample fluid is determined based at least in part on the second $CO_2$ gas (910). For example, using the laser detection arrangement illustrated in FIG. 8A, the measurement system 804 can determine a level of total urea in the sample fluid based on a level of $CO_2$ gas liberated by the interaction between the sample fluid and the conditions in the second chamber.

After one or both of the total CO2 and the total urea levels have been determined, adjustments can be made to the chemical composition of dialysate within the dialysis system. These adjustments can also be made to affect changes in the blood chemistry of a patient undergoing dialysis treatment.

In some examples, the measurement system 804 can be used to measure an amount of ammonium ($NH_4+$) in a sample fluid using a slightly different configuration. A hydrophobic membrane can be arranged in a wall of a fluid line containing the sample fluid, with a sealed chamber located on the opposite side of the membrane. Using this configuration, gas concentration will reach an equilibrium in the fluid and in the chamber on the other side of the membrane and can thus be measured by any suitable detection mechanism, such as those described above with regard to FIGS. 1-8. Alternatively, $NH_4+$ could also be measured by liberating the ammonium with an alkali solution. The alkali would stabilize the dissolved bicarbonate and produce $NH_3$ as a reaction product gas. Urea in the sample fluid would not distort the measurement of $NH_4+$, as urea is generally not reactive in the mild conditions described that would serve to liberate ammonia.

In some examples, if the sample fluid is dialysate, determining the chemical properties of the dialysate using the techniques described above can allow for the determination of certain aspects of a patient's blood chemistry. For example, if the total $CO_2$, $NH_3$, and urea are measured in a sample of dialysate, the total $CO_2$, $NH_3$, and urea can be determined for the patient's blood as well based at least in part on the measured properties of the sample dialysate.

In some examples, the extraction point for the sample fluid can affect what inferences may be drawn from the chemical properties measured in the sample fluid. For example, if dialysate is extracted near the output of a dialyzer, properties of the extracted dialysate can be used to infer chemical properties of a patient's blood. If the dialysate is extracted near the input of a dialyzer, the chemical properties of the dialysate can be used to infer a measure of the efficiency of toxin removal or the correct infusion of replacement substances such as bicarbonate. Regardless of the extraction point, adjustments in the chemical composition of the dialysate can be made based on the measured chemical properties of the extracted sample fluid.

While the condition that causes the decomposition of urea in the second chamber 818 has been described as a urease, applying a threshold level of heat and/or pressure to the sample fluid can also cause the liberation of product gases that can be used to determine the amount of urea in the sample fluid.

While the examples above describe the use of a laser 822 and a detector 824 to measure the level of $CO_2$ in a gas, other types of $CO_2$ sensors can be used to accomplish a similar effect.

While the examples above describe the pH sensor 401 as a camera or a phototransistor, the pH sensor 401 can also include one or more colorimeteric sensors. In general, a colorimeteric sensor is a semiconductor chip that senses color.

While certain implementations have been described, other implementations are possible.

In some implementations, the module 105 alternatively or additionally includes conductivity meters positioned slightly upstream of the sodium chloride container 138 and/or slightly upstream of the infusate solution container 136. These conductivity meters can be used to control the amounts of sodium chloride solution and/or infusate solution delivered to the fluid passing through the fluid outlet line 134.

Blood can also be extracted as a sample fluid from the blood component set 225 (or from another component) via a pump, and techniques similar to those described above can be used to determine bicarbonate levels of the blood, as well as other blood chemistry information. Blood can also be used as a sample fluid to determine chemical properties of dialysate within a dialysis system using techniques similar to those described above. An ultrafilter or plasmafilter may also be used to remove macromolecules and cellular materials to prevent fouling of the chemical analysis system and to assure that the $CO_2$ content measured is in the plasma, and not in the red cells.

While the external components (e.g., the sorbent device 120, the bicarbonate measurement unit 125, the bicarbonate container 191, the infusate container 136, the sodium chloride container 138, the bag 180, the dialysate bag 202, the drain container 203, and their associated fluid lines) connected to the module 105 have been described as being disposable, single use disposable components, any of these components can alternatively be reusable. For example, they can be constructed to withstand disinfection techniques, such as chlorine bleach rinses and/or other chemical rinses.

While the systems described herein have been described as including dialysate recycling modules that are connected to the dialysis machine 110, other arrangements are possible. In some implementations, for example, the various components of the module are incorporated into a single dialysis machine.

While the hemodialysis system 100 is configured so that dilution water is introduced into the dialysate before the dialysate reaches the sorbent device 120 and sodium chloride solution is introduced into the dialysate after the dialysate exits the sorbent device 120, other arrangements are possible. In certain implementations, for example, the system is configured such that the dilution water and sodium chloride solution are both introduced to the dialysate before the dialysate enters the sorbent device 120. The pumps, pump lines, and line segments associated with the delivery of the dilution water container 141 and the sodium chloride solution container 138 can, for example, be reconfigured to deliver the dilution water and sodium chloride solution to the flowing dialysate. Alternatively, lines extending from the dilution water container 141 and the sodium chloride solution container 138 can be connected to a common line via an actuated three-way valve. The three-way valve can be actuated in a manner so that as the pump associated with the pump line is operated dilution water, sodium chloride solution, or no liquid is delivered to the dialysate via the common line.

While the systems described above are configured to deliver dilution water (e.g., tap water) to dialysate before the dialysate enters the sorbent device 120 (i.e., at a pre-sorbent device location), any of the systems described herein can alternatively or additionally be configured so that dilution water is introduced to dialysate after the dialysate exits the sorbent device 120 (i.e., at a post-sorbent device location). In such implementations, the dilution water would not pass through the sorbent device 120 before being delivered to the dialyzer 135. Therefore, the dilution water in such implementations would typically be a pre-filtered or purified water, such as AAMI water.

While the systems described above use the sorbent device 120 to remove toxins from the spent dialysate, other types of devices can alternatively or additionally be used to remove toxins from the spent dialysate.

While the systems describe above describe the bicarbonate measurement unit 125 being positioned to receive dialysate just before the dialysate enters the hemodialysis machine 110, the bicarbonate measurement unit 125 can be positioned at other locations along the fluid path of the dialysate. Additionally, one or more additional bicarbonate measurement units may be provided to measure levels of bicarbonate at other points within the dialysis system 100. For example, an additional bicarbonate measurement device 125 could draw dialysate from the fluid line 258 (FIG. 2) to measure the level of bicarbonate in dialysate exiting the hemodialysis machine 110. A difference between the bicarbonate measured at fluid line 257 and fluid line 258 could then be calculated in order to determine the patient disturbance of the bicarbonate level of the dialysate (e.g., to determine the effect of a patient's blood on the dialysate). The calculated patient disturbance could be used to further alter the bicarbonate levels of the dialysate. Other chemical levels (such as total $CO_2$, $NH_3$, $NH_4+$, and/or urea/BUN) can also be altered based on the chemical levels detected using the above-mentioned techniques.

What is claimed is:

1. A method in a dialysis system comprising a carbon dioxide ($CO_2$) sensor and a pH sensor, the method comprising:
   causing the dialysate to flow into a chamber that comprises
      a gas-permeable membrane and
      a material that is configured to alter an appearance of the material based at least in part on a pH level of the dialysate, wherein the chamber is removably attached to the dialysis system;
   determining an amount of carbon dioxide ($CO_2$) in dialysate flowing through a dialysis system using a $CO_2$ sensor associated with the dialysis system;
   determining, using a pH sensor associated with the dialysis system, a pH level of the dialysate; and
   calculating a level of bicarbonate in the dialysate based at least in part on the determined amount of $CO_2$ in the dialysate and the determined pH level of the dialysate,
   wherein the pH reactive material and the gas-permeable membrane align with the pH sensor and $CO_2$ sensor respectively.

2. The method of claim 1, wherein the membrane is configured to prevent liquid from passing through the membrane.

3. The method of claim 1, wherein the $CO_2$ sensor comprises an infrared sensor.

4. The method of claim 1, further comprising causing the dialysate to contact the material.

5. The method of claim 1, wherein the material is configured to alter a color of the material based at least in part on the pH level of the dialysate.

6. The method of claim 1, wherein the material comprises a pH strip.

7. The method of claim 1, wherein the material comprises a sol-gel.

8. The method of claim 1, further comprising using the pH sensor to detect the alteration in the appearance of the material.

9. The method of claim 8, further comprising causing one or more artificial light sources to direct light toward the material such that the material reflects at least a portion of the directed light.

10. The method of claim 9, further comprising using the pH sensor to detect at least a portion of light reflected by the material.

11. The method of claim 1, wherein an amount of $CO_2$ is emitted from the dialysate, and wherein determining the amount of $CO_2$ in the dialysate comprises measuring the amount of $CO_2$ emitted from the dialysate.

12. The method of claim 1, wherein an amount of $CO_2$ is emitted from the dialysate, and wherein determining the amount of $CO_2$ in the dialysate comprises determining a partial pressure of $CO_2$ associated with a gas emitted by the dialysate.

13. The method of claim 1, wherein the pH sensor and the $CO_2$ remain free of dialysate.

14. The method of claim 1, wherein chamber further comprises a gas-collection chamber associated with the gas-permeable membrane.

15. A method comprising:
 extracting a first portion of fluid from a fluid circuit of a dialysis system comprising a $CO_2$ sensor;
 causing the first portion of fluid to flow through a first channel into a first chamber that contains a composition to liberate a first $CO_2$ gas from the first portion of fluid;
 determining a level of total $CO_2$ in the first portion of fluid based at least in part on the first $CO_2$ gas;
 extracting a second portion of fluid from the fluid circuit of the dialysis system;
 causing the second portion of fluid to flow through a second channel into a second chamber that includes conditions to liberate a second $CO_2$ gas from the second portion of fluid;
 determining a level of total urea in the second portion of fluid based at least in part on the second $CO_2$ gas; and
 calculating a net urea in the fluid based at least in part on a difference between the second $CO_2$ gas and the first $CO_2$ gas,
 wherein the first chamber and the second chamber are removably attached to the dialysis system.

16. The method of claim 15, wherein the composition comprises an acid.

17. The method of claim 16, wherein the acid comprises hydrochloric acid.

18. The method of claim 15, wherein the composition is heated to a pre-defined temperature.

19. The method of claim 15, wherein the second chamber contains a urease.

20. The method of claim 15, wherein the second chamber is heated to a desired temperature.

21. The method of claim 15, wherein determining the level of total $CO_2$ in the fluid comprises causing the first $CO_2$ gas to pass between a laser and a receiver configured to detect a beam emitted by the laser.

22. The method of claim 21, wherein the beam is emitted at a wavelength that overlaps an absorption spectrum of $CO_2$ gas but does not overlap an absorption spectrum of one or more of NH3 gas, acid gas, and water vapor.

23. The method of claim 15, wherein determining the amount of total urea in the fluid comprises causing the second $CO_2$ gas to pass between a laser and a receiver configured to detect a beam emitted by the laser.

24. The method of claim 23, wherein the beam is emitted at a wavelength that overlaps an absorption spectrum of $CO_2$ gas but does not overlap an absorption spectrum of one or more of NH3 gas, acid gas, and water vapor.

25. The method of claim 15, further comprising:
 heating the first portion of the fluid or the second portion of the fluid in the first or second channel, respectively, to liberate NH3 gas; and
 determining an amount of NH3 in the fluid based at least in part on the NH3 gas.

26. The method of claim 25, wherein determining an amount of NH3 in the fluid comprises causing the NH3 gas to pass between a laser and a receiver configured to detect a beam emitted by the laser.

27. The method of claim 26, wherein the beam is emitted at a wavelength that overlaps an absorption spectrum of NH3 gas but does not overlap an absorption spectrum of $CO_2$ gas.

28. The method of claim 15, wherein extracting at least one of the first and second portions of fluid from the fluid circuit of the dialysis system comprises using a peristaltic pump to extract at least one of the first and second portions of the fluid from a fluid line associated with the fluid circuit.

29. The method of claim 15, wherein the first and second portions of fluid comprise dialysate.

30. The method of claim 15, wherein the first and second portions of fluid comprise blood.

31. The method of claim 15, wherein extracting the fluid does not interrupt a dialysis treatment session being performed by the dialysis system.

32. The method of claim 15, wherein the dialysis system is a hemodialysis system.

33. The method of claim 15, wherein the first and second portions of fluid are extracted in a single extraction.

34. The method of claim 15, wherein the first portion of fluid does not flow into the second chamber.

35. A dialysis system comprising:
 a dialysis machine comprising a pH sensor and a $CO_2$ sensor; and
 a dialysis fluid chamber configured to be removably attached to the dialysis machine, the dialysis fluid chamber comprising:
  a housing defining an inlet port, an outlet port, a dialysis fluid passage extending between the inlet and outlet ports, and first and second apertures adjacent the fluid passage,
  a pH reactive material disposed over the first aperture of the housing; and
  a gas-permeable membrane disposed over the second aperture of the housing,
 wherein the pH reactive material and the gas-permeable membrane align with the pH sensor and $CO_2$ sensor, respectively, when the dialysis fluid chamber is connected to the dialysis machine such that the pH sensor and $CO_2$ sensor can be used to detect a pH level and $CO_2$ level, respectively, of a dialysis fluid flowing through the dialysis fluid chamber.

36. A dialysis fluid chamber comprising
 a housing defining an inlet port, an outlet port, a dialysis fluid passage extending between the inlet and outlet ports, and first and second apertures adjacent the fluid passage,
 a pH reactive material disposed over the first aperture of the housing; and
 a gas-permeable membrane disposed over the second aperture of the housing,
 wherein the housing is configured such that the pH reactive material and the gas-permeable membrane align with a pH sensor and $CO_2$ sensor, respectively, of a dialysis system when the dialysis fluid chamber is connected to the dialysis system,
 wherein the housing is removably attached to the dialysis system.

37. A dialysis system comprising:
a dialysis machine comprising a sensor; and
a gas emission device configured to be connected to the dialysis machine in a manner such that dialysis fluid can be forced into the gas emission device, the gas emission device comprising:
- a housing defining first and second chambers; and
- a member defining a first fluid passage leading to the first chamber and a second fluid passage leading to the second chamber, at least one of the first and second fluid passages being heated such that dialysis fluid flowing along the at least one of the first and second fluid passages is heated to a desired temperature, wherein the first chamber contains an acid that causes $CO_2$ to be emitted from dialysis fluid that is delivered to the first chamber via the first fluid passage, the second chamber can cause a gas to be emitted from dialysis fluid that is delivered to the second chamber via the second fluid passage, and the sensor is configured to detect an amount of $CO_2$ emitted from the dialysis fluid delivered to the first chamber and to detect an amount of the gas emitted from the dialysis fluid delivered to the second chamber, and wherein the housing is removably attached to the dialysis system.

38. The dialysis system of claim 37, wherein the second chamber contains a urease.

39. The dialysis system of claim 37, wherein the second chamber is heated to a desired temperature.

40. The dialysis system of claim 37, wherein the gas emitted from the dialysis fluid delivered to the second chamber is $CO_2$.

41. The dialysis system of claim 37, wherein the gas emitted from the dialysis fluid delivered to the second chamber is NH3.

42. The dialysis system of claim 37, wherein the dialysis machine further comprises a microprocessor in communication with the pH sensor and the $CO_2$ sensor, the microprocessor being programmed to determine a level of bicarbonate in the dialysis fluid based at least in part on the detected pH and $CO_2$ levels.

43. The dialysis system of claim 37, further comprising a dialysis fluid inlet line that can be selectively placed in fluid communication with the first chamber or the second chamber, and a pump connected to the dialysis fluid inlet line, the pump being operable to force fluid into the gas emission device via the dialysis fluid inlet line.

44. The dialysis system of claim 43, wherein the dialysis fluid inlet line is connected to a dialysate line of the dialysis system such that dialysate can be delivered to the gas emission device via the dialysis fluid inlet line.

45. The dialysis system of claim 44, wherein the dialysis fluid inlet line is connected to a blood line of the dialysis system such that blood can be delivered to the gas emission device via the dialysis fluid inlet line.

46. The dialysis system of claim 37, wherein the first fluid passage does not lead to the second chamber.

47. A gas emission device configured to be connected to a dialysis machine in a manner such that dialysis fluid can be forced into the gas emission device, the gas emission device comprising:
- a housing defining first and second chambers, and
- a member defining a first fluid passage leading to the first chamber and a second fluid passage leading to the second chamber, at least one of the first and second fluid passages being heated such that dialysis fluid flowing along the at least one of the first and second fluid passages is heated to a desired temperature, wherein the first chamber contains an acid that causes $CO_2$ to be emitted from dialysis fluid that is delivered to the first chamber via the first fluid passage, the second chamber can cause a gas to be emitted from dialysis fluid that is delivered to the second chamber via the second fluid passage, and the gas emission device defines a flute portion that is positioned adjacent a sensor of the dialysis machine when the gas emission device is connected to the dialysis machine, wherein the housing is removably attached to the dialysis machine.

48. A method comprising:
extracting a first portion of fluid from a fluid circuit of a dialysis system;
causing the first portion of fluid to flow through a first channel into a first chamber that contains a composition to liberate a $CO_2$ gas from the first portion of fluid;
determining a level of total $CO_2$ in the first portion of fluid based at least in part on the $CO_2$ gas;
extracting a second portion of fluid from the fluid circuit of the dialysis system;
causing the second portion of the first portion of fluid to flow through a second channel into a second chamber to liberate a $NH_3$ gas from the second portion of fluid; and
determining a level of total urea in the second portion of fluid based at least in part on the $NH_3$ gas,
wherein the first chamber and the second chamber are removably attached to the dialysis system.

49. The method of claim 48, wherein the first portion of fluid does not flow into the second chamber.

* * * * *